US009555221B2

(12) United States Patent
Koehler et al.

(10) Patent No.: US 9,555,221 B2
(45) Date of Patent: Jan. 31, 2017

(54) CONSTANT FORCE HOLD TIP PROTECTOR FOR A SAFETY CATHETER

(71) Applicant: Smiths Medical ASD, Inc., Rockland, MA (US)

(72) Inventors: Thomas T. Koehler, Simsbury, CT (US); Gerard Libby, Wakefield, MA (US)

(73) Assignee: SMITHS MEDICAL ASD, INC., Rockland, MA (US)

(*) Notice: Subject to any disclaimer, the term of this patent is extended or adjusted under 35 U.S.C. 154(b) by 109 days.

(21) Appl. No.: 14/250,042

(22) Filed: Apr. 10, 2014

(65) Prior Publication Data

US 2015/0290430 A1 Oct. 15, 2015

(51) Int. Cl.
*A61M 25/06* (2006.01)
*A61M 5/162* (2006.01)
*A61M 5/32* (2006.01)

(52) U.S. Cl.
CPC ....... *A61M 25/0618* (2013.01); *A61M 5/1626* (2013.01); *A61M 5/329* (2013.01); *A61M 25/0606* (2013.01); *A61M 25/0631* (2013.01)

(58) Field of Classification Search
CPC ............ A61M 25/0618; A61M 5/3273; A61M 25/0606; A61M 5/1626; A61M 25/0612; A61M 5/321; A61M 5/329
See application file for complete search history.

(56) References Cited

U.S. PATENT DOCUMENTS

| 1,085,505 A | | 1/1914 | Stafford |
| 3,055,364 A | | 9/1962 | Myerson et al. |
| 3,477,437 A | | 11/1969 | Goldberg |
| 3,666,373 A | * | 5/1972 | Reed ............... B43K 23/126 401/247 |

(Continued)

FOREIGN PATENT DOCUMENTS

| CA | 2033361 A1 | 6/1992 |
| CN | 1547493 A | 11/2004 |

(Continued)

OTHER PUBLICATIONS

European Patent Office, International Search Report and Written Opinion issued in International Application No. PCT/US2015/023519 dated Jul. 16, 2015.

(Continued)

*Primary Examiner* — Kevin C Sirmons
*Assistant Examiner* — William Carpenter
(74) *Attorney, Agent, or Firm* — Snell & Wilmer L.L.P.

(57) ABSTRACT

A tip protector for a safety catheter includes an outer member releasably engaged with the interior cavity of the catheter hub. The outer member includes a generally fixed radially outwardly projecting portion to provide a holding force, and an inner member axially shiftably received within the outer member. A needle cannula received in the inner and outer members is operable to axially shift the inner member between a distal position wherein the distal tip extends distally of the tip protector, and a proximal position wherein the distal tip is within the outer member. The holding force of the outer member to the interior wall of the catheter hub remains substantially constant irrespective of the position of the inner member between the distal and proximal positions.

24 Claims, 20 Drawing Sheets

(56) References Cited

U.S. PATENT DOCUMENTS

| | | | |
|---|---|---|---|
| 3,680,562 | A * | 8/1972 | Wittes ............... A61M 25/0606 604/174 |
| 4,425,120 | A | 1/1984 | Sampson et al. |
| 4,755,170 | A | 7/1988 | Golden |
| 4,778,453 | A | 10/1988 | Lopez |
| 4,781,692 | A | 11/1988 | Jagger et al. |
| 4,795,432 | A | 1/1989 | Karczmer |
| 4,804,371 | A | 2/1989 | Vaillancourt |
| 4,834,718 | A | 5/1989 | McDonald |
| 4,846,805 | A | 7/1989 | Sitar |
| 4,887,998 | A | 12/1989 | Martin et al. |
| 4,921,490 | A | 5/1990 | Spier et al. |
| 4,929,241 | A | 5/1990 | Kulli |
| 4,944,725 | A * | 7/1990 | McDonald ........ A61M 25/0631 604/164.08 |
| 4,944,728 | A | 7/1990 | Carrell et al. |
| 4,952,207 | A | 8/1990 | Lemieux |
| 4,964,854 | A | 10/1990 | Luther |
| 4,994,041 | A | 2/1991 | Dombrowski et al. |
| 5,059,180 | A | 10/1991 | McLees |
| 5,085,648 | A | 2/1992 | Purdy et al. |
| 5,092,851 | A | 3/1992 | Ragner |
| 5,102,394 | A | 4/1992 | Lasaitis et al. |
| 5,108,379 | A | 4/1992 | Dolgin et al. |
| 5,129,884 | A | 7/1992 | Dysarz |
| 5,135,504 | A | 8/1992 | McLees |
| 5,156,599 | A | 10/1992 | Ranford et al. |
| 5,183,468 | A | 2/1993 | McLees |
| 5,205,829 | A | 4/1993 | Lituchy |
| 5,215,525 | A * | 6/1993 | Sturman ........... A61M 25/0631 604/164.08 |
| 5,215,528 | A | 6/1993 | Purdy et al. |
| 5,217,438 | A | 6/1993 | Davis et al. |
| RE34,416 | E | 10/1993 | Lemieux |
| 5,269,765 | A | 12/1993 | Kuracina |
| 5,279,591 | A | 1/1994 | Simon |
| 5,295,963 | A | 3/1994 | Deeks |
| 5,300,039 | A | 4/1994 | Poulsen |
| 5,300,045 | A | 4/1994 | Plassche, Jr. |
| 5,306,259 | A | 4/1994 | Fischell et al. |
| 5,322,517 | A | 6/1994 | Sircom et al. |
| 5,328,482 | A | 7/1994 | Sircom et al. |
| 5,330,432 | A | 7/1994 | Yoon |
| 5,334,158 | A | 8/1994 | McLees |
| 5,336,199 | A | 8/1994 | Castillo et al. |
| 5,344,408 | A | 9/1994 | Partika |
| 5,364,370 | A | 11/1994 | Szerlip et al. |
| 5,376,080 | A | 12/1994 | Petrussa |
| 5,409,461 | A | 4/1995 | Steinman |
| 5,419,766 | A | 5/1995 | Chang et al. |
| 5,423,766 | A | 6/1995 | Di Cesare |
| 5,458,658 | A | 10/1995 | Sircom |
| 5,466,223 | A | 11/1995 | Bressler et al. |
| 5,472,430 | A | 12/1995 | Vaillancourt et al. |
| 5,478,313 | A | 12/1995 | White |
| 5,522,835 | A * | 6/1996 | Tovey ................... A61M 29/02 604/104 |
| 5,533,974 | A | 7/1996 | Gaba |
| 5,558,651 | A | 9/1996 | Crawford et al. |
| 5,569,202 | A | 10/1996 | Kovalic et al. |
| 5,584,809 | A | 12/1996 | Gaba |
| 5,584,810 | A | 12/1996 | Brimhall |
| 5,599,310 | A * | 2/1997 | Bogert ............... A61M 25/0625 604/164.12 |
| 5,601,532 | A | 2/1997 | Gaba |
| 5,601,536 | A | 2/1997 | Crawford et al. |
| 5,611,781 | A | 3/1997 | Sircom et al. |
| 5,613,500 | A | 3/1997 | Bishop |
| 5,662,610 | A | 9/1997 | Sircom |
| 5,665,072 | A | 9/1997 | Yoon |
| 5,676,656 | A | 10/1997 | Brimhall |
| 5,676,658 | A | 10/1997 | Erskine |
| 5,690,619 | A | 11/1997 | Erskine |
| 5,695,474 | A | 12/1997 | Daugherty |
| 5,697,907 | A | 12/1997 | Gaba |
| 5,718,688 | A | 2/1998 | Wozencroft |
| 5,738,660 | A | 4/1998 | Luther |
| 5,743,891 | A | 4/1998 | Tolkoff et al. |
| 5,769,827 | A | 6/1998 | DeMichele et al. |
| 5,795,336 | A | 8/1998 | Romano et al. |
| 5,800,395 | A | 9/1998 | Botich et al. |
| 5,800,404 | A | 9/1998 | Poulsen |
| 5,817,070 | A | 10/1998 | Tamaro |
| 5,830,189 | A | 11/1998 | Chang |
| 5,853,393 | A | 12/1998 | Bogert |
| 5,865,806 | A | 2/1999 | Howell |
| 5,879,337 | A | 3/1999 | Kuracina et al. |
| 5,882,337 | A | 3/1999 | Bogert et al. |
| 5,882,342 | A | 3/1999 | Cooper et al. |
| 5,893,845 | A | 4/1999 | Newby et al. |
| 5,911,705 | A | 6/1999 | Howell |
| 5,919,168 | A | 7/1999 | Wheeler |
| 5,935,109 | A | 8/1999 | Donnan |
| 5,937,605 | A | 8/1999 | Wendt |
| 6,001,080 | A | 12/1999 | Kuracina et al. |
| 6,004,294 | A | 12/1999 | Brimhall et al. |
| 6,007,244 | A | 12/1999 | Dinder |
| 6,077,244 | A | 6/2000 | Botich et al. |
| 6,096,005 | A | 8/2000 | Botich et al. |
| 6,117,108 | A | 9/2000 | Woehr et al. |
| 6,203,527 | B1 | 3/2001 | Zadini et al. |
| 6,210,374 | B1 | 4/2001 | Malencheck |
| 6,213,978 | B1 | 4/2001 | Voyten |
| 6,221,047 | B1 | 4/2001 | Greene et al. |
| 6,228,054 | B1 | 5/2001 | Dysarz |
| 6,280,419 | B1 | 8/2001 | Vojtasek |
| 6,287,278 | B1 | 9/2001 | Woehr et al. |
| 6,298,623 | B1 | 10/2001 | Wendt |
| 6,322,537 | B1 | 11/2001 | Chang |
| 6,379,333 | B1 | 4/2002 | Brimhall et al. |
| 6,443,927 | B1 | 9/2002 | Cook |
| 6,443,929 | B1 | 9/2002 | Kuracina et al. |
| 6,511,461 | B2 | 1/2003 | Jonsson |
| 6,524,278 | B1 | 2/2003 | Campbell et al. |
| 6,544,231 | B1 | 4/2003 | Palmer et al. |
| 6,547,762 | B1 | 4/2003 | Botich et al. |
| 6,547,764 | B2 | 4/2003 | Larsen et al. |
| 6,558,354 | B1 | 5/2003 | Howell |
| 6,582,402 | B1 | 6/2003 | Erskine |
| 6,595,954 | B1 * | 7/2003 | Luther ............... A61M 25/0618 604/110 |
| 6,595,955 | B2 | 7/2003 | Ferguson et al. |
| 6,616,630 | B1 | 9/2003 | Woehr et al. |
| 6,623,458 | B2 | 9/2003 | Woehr et al. |
| 6,629,957 | B1 | 10/2003 | Wiklund |
| 6,629,959 | B2 | 10/2003 | Kuracina et al. |
| 6,632,198 | B2 | 10/2003 | Caizza |
| 6,652,486 | B2 | 11/2003 | Bialecki et al. |
| 6,652,490 | B2 | 11/2003 | Howell |
| 6,673,044 | B2 | 1/2004 | Righi et al. |
| 6,689,102 | B2 * | 2/2004 | Greene ............... A61M 25/0625 604/164.07 |
| 6,695,814 | B2 | 2/2004 | Greene et al. |
| 6,706,019 | B1 | 3/2004 | Parker et al. |
| 6,709,419 | B2 | 3/2004 | Woehr |
| 6,712,787 | B1 | 3/2004 | Dysarz |
| 6,716,197 | B2 | 4/2004 | Svendsen |
| 6,726,658 | B2 | 4/2004 | Hochman |
| 6,732,991 | B1 | 5/2004 | Zakrzewski et al. |
| 6,749,588 | B1 | 6/2004 | Howell et al. |
| 6,776,777 | B2 | 8/2004 | Barrelle |
| 6,786,875 | B2 | 9/2004 | Barker et al. |
| 6,796,962 | B2 | 9/2004 | Ferguson et al. |
| 6,811,545 | B2 | 11/2004 | Vaillancourt |
| 6,860,871 | B2 | 3/2005 | Kuracina et al. |
| 6,869,415 | B2 | 3/2005 | Asbaghi |
| 6,872,193 | B2 | 3/2005 | Shaw et al. |
| 6,902,546 | B2 | 6/2005 | Ferguson |
| 6,905,478 | B2 | 6/2005 | Ingram et al. |
| 6,972,002 | B2 | 12/2005 | Thorne |
| RE38,996 | E | 2/2006 | Crawford et al. |
| 6,994,690 | B2 | 2/2006 | Kiehne |
| 7,004,927 | B2 | 2/2006 | Ferguson et al. |

(56) References Cited

U.S. PATENT DOCUMENTS

| | | |
|---|---|---|
| 7,008,402 B2 | 3/2006 | Ferguson et al. |
| 7,014,622 B1 | 3/2006 | Pressly, Sr. et al. |
| 7,014,623 B2 | 3/2006 | Prestidge et al. |
| 7,018,344 B2 | 3/2006 | Bressler et al. |
| 7,041,086 B2 | 5/2006 | Yang |
| 7,041,092 B2 | 5/2006 | Barrelle |
| 7,083,600 B2 | 8/2006 | Meloul |
| 7,125,397 B2 | 10/2006 | Woehr et al. |
| 7,172,576 B2 | 2/2007 | Sawa et al. |
| 7,201,740 B2 | 4/2007 | Crawford |
| 7,214,211 B2 | 5/2007 | Woehr et al. |
| 7,220,247 B2 | 5/2007 | Shaw et al. |
| 7,238,169 B2 | 7/2007 | Takagi et al. |
| 7,255,689 B2 | 8/2007 | Westbye |
| 7,300,416 B2 | 11/2007 | Botich et al. |
| 7,344,517 B2 | 3/2008 | Schiller |
| 7,347,838 B2 | 3/2008 | Kulli |
| 7,354,422 B2 | 4/2008 | Riesenberger et al. |
| 7,393,344 B2 | 7/2008 | Mohammed |
| 7,597,681 B2 | 10/2009 | Sutton et al. |
| 7,632,243 B2 | 12/2009 | Bialecki et al. |
| 7,658,725 B2 | 2/2010 | Bialecki et al. |
| 7,753,877 B2 | 7/2010 | Bialecki et al. |
| 7,785,296 B2 | 8/2010 | Muskatello et al. |
| 7,828,774 B2 | 11/2010 | Harding et al. |
| 8,162,881 B2 | 4/2012 | Lilley, Jr. et al. |
| 8,257,322 B2 | 9/2012 | Koehler et al. |
| 8,512,295 B2 * | 8/2013 | Evans .............. A61M 5/3202 215/216 |
| 2002/0169418 A1 | 11/2002 | Menzi et al. |
| 2002/0193745 A1 | 12/2002 | Ferguson |
| 2003/0018303 A1 * | 1/2003 | Sharp .............. A61M 5/3202 604/192 |
| 2003/0060771 A1 | 3/2003 | Bialecki et al. |
| 2003/0100868 A1 | 5/2003 | Ferguson et al. |
| 2003/0144627 A1 | 7/2003 | Woehr et al. |
| 2003/0199827 A1 | 10/2003 | Thorne |
| 2004/0019332 A1 | 1/2004 | Grabis et al. |
| 2004/0030294 A1 | 2/2004 | Mahurkar |
| 2004/0049155 A1 | 3/2004 | Schramm |
| 2004/0078003 A1 | 4/2004 | Smith et al. |
| 2004/0092889 A1 | 5/2004 | Ferguson et al. |
| 2004/0097887 A1 | 5/2004 | Secrest et al. |
| 2004/0116854 A1 | 6/2004 | Abulhaj et al. |
| 2004/0122373 A1 | 6/2004 | Botich et al. |
| 2004/0186434 A1 | 9/2004 | Harding et al. |
| 2004/0204681 A1 | 10/2004 | Thoresen et al. |
| 2004/0225260 A1 | 11/2004 | Villa et al. |
| 2004/0236288 A1 | 11/2004 | Howell et al. |
| 2005/0027263 A1 | 2/2005 | Woehr et al. |
| 2005/0038384 A1 | 2/2005 | Li |
| 2005/0075609 A1 * | 4/2005 | Latona .............. A61M 5/3273 604/164.08 |
| 2005/0080378 A1 | 4/2005 | Cindrich et al. |
| 2005/0096592 A1 | 5/2005 | Carlyon et al. |
| 2005/0107740 A1 | 5/2005 | Jensen et al. |
| 2005/0113750 A1 | 5/2005 | Targell |
| 2005/0113755 A1 | 5/2005 | Greene et al. |
| 2005/0159705 A1 | 7/2005 | Crawford et al. |
| 2005/0182362 A1 | 8/2005 | Sircom et al. |
| 2005/0182363 A1 | 8/2005 | Kulli |
| 2005/0277879 A1 | 12/2005 | Daga |
| 2006/0089597 A1 | 4/2006 | Allard |
| 2006/0100588 A1 | 5/2006 | Brunnberg et al. |
| 2006/0116638 A1 | 6/2006 | Woehr et al. |
| 2007/0038184 A1 | 2/2007 | Bialecki et al. |
| 2007/0038185 A1 | 2/2007 | Albert et al. |
| 2007/0038188 A1 * | 2/2007 | Bialecki .............. A61M 25/0618 604/164.08 |
| 2007/0073222 A1 | 3/2007 | Lilley et al. |
| 2007/0112305 A1 | 5/2007 | Brimhall |
| 2007/0129674 A1 | 6/2007 | Liversidge |
| 2007/0191775 A1 * | 8/2007 | Diep .............. A61M 25/0097 604/164.01 |
| 2007/0191776 A1 * | 8/2007 | Bialecki .............. A61M 25/0631 604/164.08 |
| 2007/0191777 A1 | 8/2007 | King |
| 2008/0249478 A1 | 10/2008 | Ishikura et al. |
| 2009/0182280 A1 | 7/2009 | Glowacki et al. |
| 2009/0259194 A1 * | 10/2009 | Pinedjian .............. A61M 5/002 604/192 |
| 2009/0281499 A1 * | 11/2009 | Harding .............. A61M 25/0618 604/164.08 |
| 2009/0312711 A1 * | 12/2009 | Brimhall .............. A61M 25/0618 604/164.08 |
| 2010/0016804 A1 * | 1/2010 | Muskatello ......... A61M 5/3273 604/198 |
| 2010/0049139 A1 * | 2/2010 | Kiyono .............. A61M 5/158 604/180 |
| 2010/0168675 A1 | 7/2010 | Cindrich et al. |
| 2010/0222746 A1 | 9/2010 | Burkholz |
| 2010/0222749 A1 * | 9/2010 | Baid .............. A61M 5/3273 604/263 |
| 2010/0241087 A1 | 9/2010 | Moulton |
| 2011/0213307 A1 | 9/2011 | Kawai et al. |
| 2011/0301551 A1 * | 12/2011 | Koehler .............. A61M 5/1626 604/263 |
| 2012/0296282 A1 | 11/2012 | Koehler et al. |
| 2014/0039399 A1 | 2/2014 | Burkholz |
| 2014/0276453 A1 | 9/2014 | Woehr |

FOREIGN PATENT DOCUMENTS

| | | |
|---|---|---|
| CN | 101500637 A | 8/2009 |
| CN | 101543657 A | 9/2009 |
| EP | 0367549 A2 | 5/1990 |
| EP | 0554841 A1 | 8/1993 |
| EP | 0747085 A2 | 12/1996 |
| EP | 0750916 A2 | 1/1997 |
| EP | 0832666 A2 | 4/1998 |
| EP | 1378263 A2 | 1/2004 |
| EP | 1974765 | 10/2008 |
| EP | 2343095 | 7/2011 |
| JP | H0724071 | 1/1995 |
| JP | 2001190683 A | 7/2001 |
| JP | 2002210005 A | 7/2002 |
| JP | 2004-073403 A | 3/2004 |
| JP | 2004113394 A | 4/2004 |
| JP | 2004113523 A | 4/2004 |
| JP | 2004113524 A | 4/2004 |
| JP | 2004154364 A | 6/2004 |
| JP | 2004321489 A | 11/2004 |
| WO | 9008564 A1 | 8/1990 |
| WO | 93/25254 A1 | 12/1993 |
| WO | 9908742 A1 | 2/1999 |
| WO | 0006221 A1 | 2/2000 |
| WO | 0123028 A1 | 4/2001 |
| WO | 0123029 | 4/2001 |
| WO | 0168174 | 9/2001 |
| WO | 0193940 | 12/2001 |
| WO | 03011381 | 2/2003 |
| WO | 04/000408 A1 | 12/2003 |
| WO | 03103757 A1 | 12/2003 |
| WO | 2004043521 A1 | 5/2004 |
| WO | 2005087306 A1 | 9/2005 |
| WO | 2006062983 | 6/2006 |
| WO | 2007018824 A2 | 2/2007 |
| WO | 2008/021132 A1 | 2/2008 |
| WO | 2009/010847 A2 | 1/2009 |
| WO | 2009139951 | 11/2009 |
| WO | 2009154824 | 12/2009 |
| WO | 2010008784 | 1/2010 |
| WO | 2010038471 A1 | 4/2010 |
| WO | 2010101740 | 9/2010 |
| WO | 2010/127846 A1 | 11/2010 |
| WO | 2011/036574 A1 | 3/2011 |

OTHER PUBLICATIONS

International Search Report for WO 2007/018824, mailed on Jun. 9, 2007.

(56) References Cited

OTHER PUBLICATIONS

Extended European Search Report and Opinion for EP 06253995.2, mailed on Jan. 24, 2007 (6 pages).
International Search Report and Written Opinion received in counterpart International Patent Application PCT/US2009/04809 mailed Jan. 20, 2010 (9 pages).
Extended European Search Report from the EPO in counterpart EP Application No. 14 161 101.2 dated Apr. 14, 2014 (9 pages).
Japanese Patent Office, Office Action issued in corresponding Japanese Application No. 2013-513163, dated Aug. 1, 2014, 3 pages.
The Patent Office of the People's Republic of China, Official Action issued in Application No. 201180020786.8 dated Sep. 4, 2014.
The Patent Office of the People's Republic of China, Official Action issued in Application No. 201180020786.8 dated Apr. 3, 2015.
European Patent Office, International Preliminary Report on Patentability issued in International Application No. PCT/US2011/028770 dated Aug. 21, 2012.
IP Australia, Examination Report issued in Application No. 2011261837 dated May 5, 2015.
Korean Intellectual Property Office, Notice of Preliminary Rejection issued in Application No. 10-2011-7001246 dated Apr. 21, 2015.
European Patent Office, extended European Search Report issued in Application No. 09798452.0 dated Feb. 7, 2013.
State Intellectual Property Office of the People's Republic of China, Official Action issued in Application No. 2009801280721 dated Aug. 31, 2012.
State Intellectual Property Office of the People's Republic of China, Official Action issued in Application No. 2009801280721 dated Dec. 9, 2013.
Canadian Intellectual Property Office, Official Action issued in Application No. 2,723,093 dated May 20, 2015.
IP Australia, Examination Report issued in Application No. 2009271370 dated Feb. 21, 2013.
European Patent Office, International Search Report issued in International Application No. PCT/US2011/028770 dated May 19, 2011.

\* cited by examiner

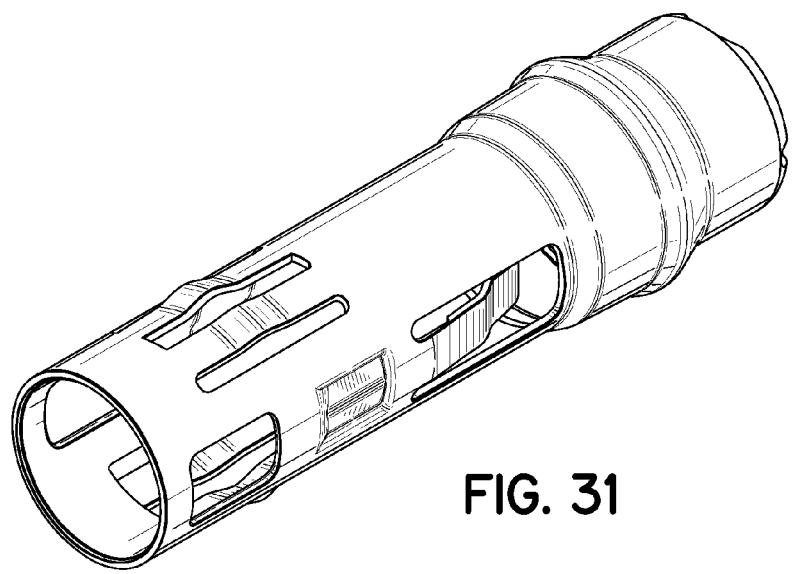
FIG. 31
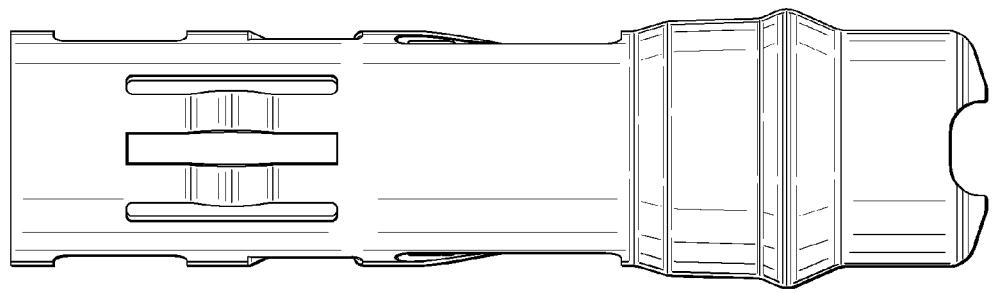
FIG. 32
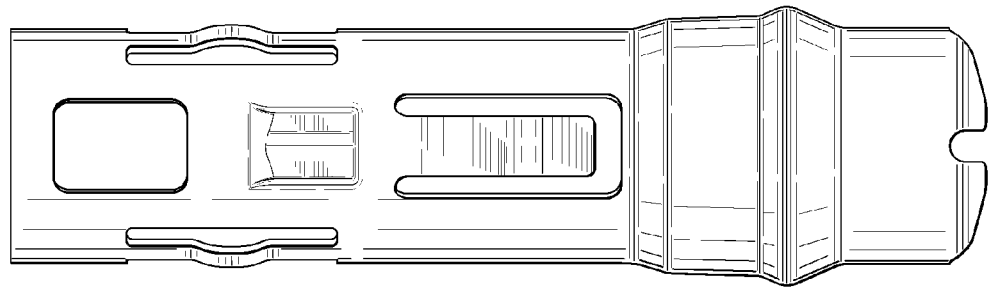
FIG. 33
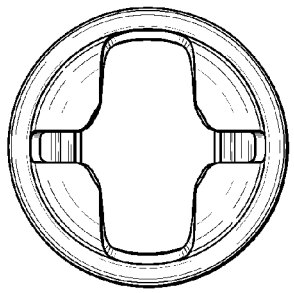 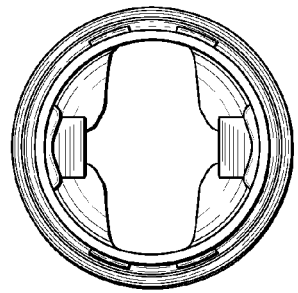
FIG. 34  FIG. 35

CONSTANT FORCE HOLD TIP PROTECTOR FOR A SAFETY CATHETER

TECHNICAL FIELD

The present invention relates to safety catheters and, more particularly, to tip protectors to shield the sharp tip of the needle cannula used with the catheter.

BACKGROUND

Safety catheters are widely used and typically include a catheter hub with a catheter tube extending distally thereof to be placed intravenously, a needle hub or support with a needle cannula extending distally thereof to a sharp distal tip and extending through the catheter tube to expose the sharp tip in order to facilitate intravenous insertion of the catheter tube, and a tip protector through which at least a portion of the needle shaft passes and adapted to enclose or otherwise shield the tip of the needle cannula after it has been withdrawn from the catheter tube and into the tip protector. The tip protector may also include a flexing feature which selectively engages the catheter hub to hold the tip protector to the catheter hub in a ready position with the sharp tip exposed and to readily come away from the catheter hub in a fired position with the sharp tip enclosed by the tip protector.

One type of design for the tip protector involves two axially shiftable components, one being an outer member which includes the catheter hub engagement feature and the other being an inner member which, in the ready position has the needle shaft passing therethrough, and in the fired position is closed down over the sharp tip. In that type of design, the inner member is positioned to block the catheter hub engagement feature in the ready position but when axially shifted into the fired position moves away from blocking the engagement feature of the outer member. In the ready position, the inner member limits the ability of the catheter hub engagement feature to flex radially inwardly and release engagement with the catheter hub such that the force required to remove the tip protector from the catheter hub is very high in the ready position. With such axially shiftable members, the needle cannula engages with the inner member as the sharp tip is pulled proximally toward and into the confines of the inner member to cause the inner member to slide axially relative to the outer member and into the fired position. In the fired position, the engagement feature of the outer member is no longer blocked by the inner member such that the engagement feature is able to flex (either due to its own bias or by interaction with the catheter hub) radially inwardly to come away from the catheter hub with relatively lower force, which is accomplished by further proximal movement of the needle cannula translating force from the inner member to the outer member to pull the tip protector proximally out of the catheter hub.

SUMMARY

The present invention provides a tip protector in which the position of the inner member does not control the force levels required to remove the tip protector from the catheter hub. To that end, and in accordance with the principles of the present invention, the catheter hub engagement feature is a generally fixed radially outwardly projecting portion of the outer member. Removal of the tip protector is understood to require plastic deformation of the catheter hub as the fixed projecting portion tries to overcome the holding force thereon, rather than radially inward flexing of the engagement feature. The result is that the holding force of the outer member to the catheter hub remains substantially constant irrespective of the position of the inner member. Moreover, forming an outer member with such a flexing member is complicated, whereas the fixed nature of the engagement feature of the present invention makes formation of the outer member less complicated. Additionally, issues involved in the interplay between the inner and outer members that must be taken into account with a flexing member are eliminated, or at least substantially reduced. This, too, simplifies the manufacture of the tip protector and may simplify its use.

BRIEF DESCRIPTION OF THE DRAWING

The accompanying drawings, which are incorporated in and constitute a part of this specification, illustrate embodiments of the invention and, together with the general description given above and the detailed description of the embodiments given below, serve to explain the principles of the invention.

FIGS. 31-35 show various views of an alternative embodiment of the outer member, with FIG. 31 being a perspective view, FIG. 32 being a top view the bottom view being a mirror image thereof, FIG. 33 being a left side view the right side view being a mirror image thereof, FIG. 34 being a proximal end view, and FIG. 35 being a distal end view.

DETAILED DESCRIPTION

Figure 1:
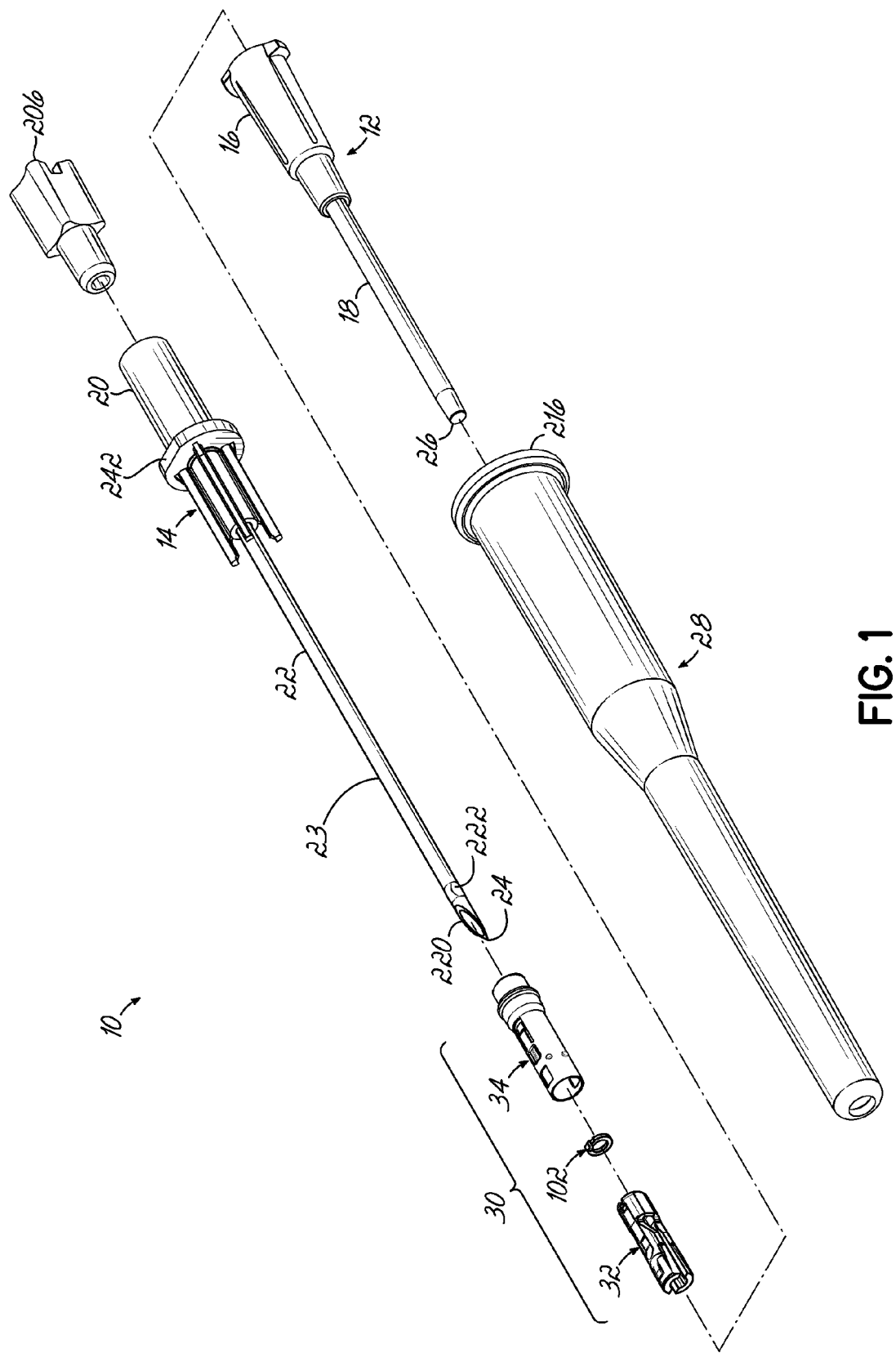
FIG. 1 is a disassembled perspective view of a safety catheter in accordance with one embodiment of the invention.
Figure 2:
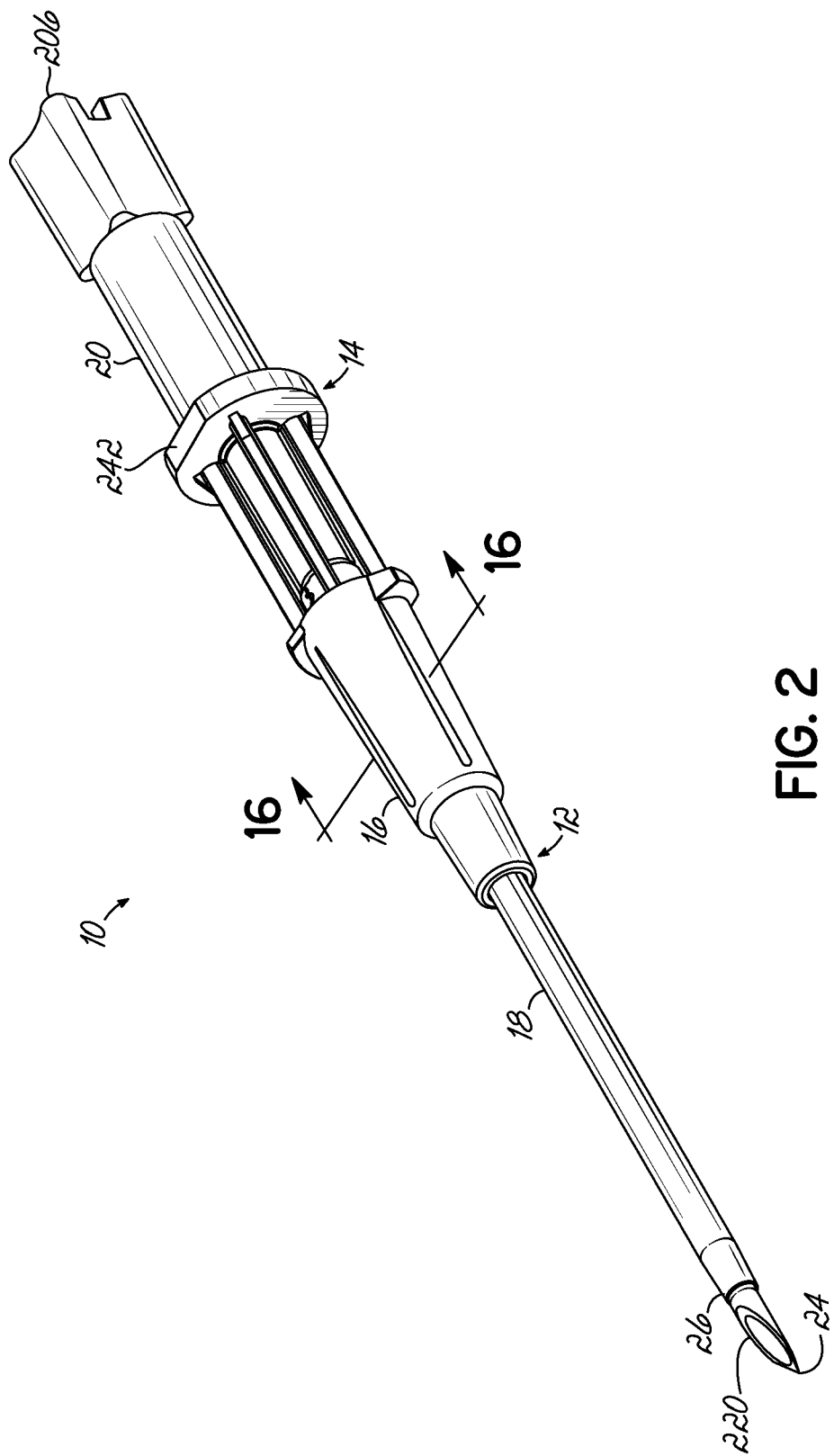
FIG. 2 is an assembled perspective view of the safety catheter shown in FIG. 1, but without the protective sheath.

In reference to FIGS. 1 and 2, a peripheral intravenous safety catheter 10 includes a catheter assembly 12 and a needle assembly 14 nested relative to the catheter assembly 12 and configured to provide an interface with the vasculature of a patient (not shown). The catheter assembly 12 includes a catheter hub 16 and a generally flexible catheter tube 18 coupled to a distal portion of the catheter hub 16 and extending distally thereof. The needle assembly 14 includes a needle support or hub 20 and a needle cannula 22 coupled to a distal portion of the needle hub 20 with a needle shaft 23 extending distally of the needle hub 20. As is generally conventional, the needle assembly 14 is positioned relative to the catheter assembly 12 such that the needle cannula 22 is disposed within the catheter tube 18 and a distal tip 24 thereof (which in the embodiment shown is sharp but could alternatively be blunt) extends beyond a distal end 26 of the catheter tube 18 in a ready position, as illustrated in FIG. 2.

A sheath 28 may be provided to protect the safety catheter 10 prior to use, such as during transit to and storage in a medical facility. As will be discussed in more detail below, safety catheter 10 includes an exemplary tip protector 30 in accordance with various aspects of the present invention configured to protect the distal tip 24 of the needle cannula 22 when the needle cannula 22 is withdrawn from the catheter hub 16 during use.

Figure 19:
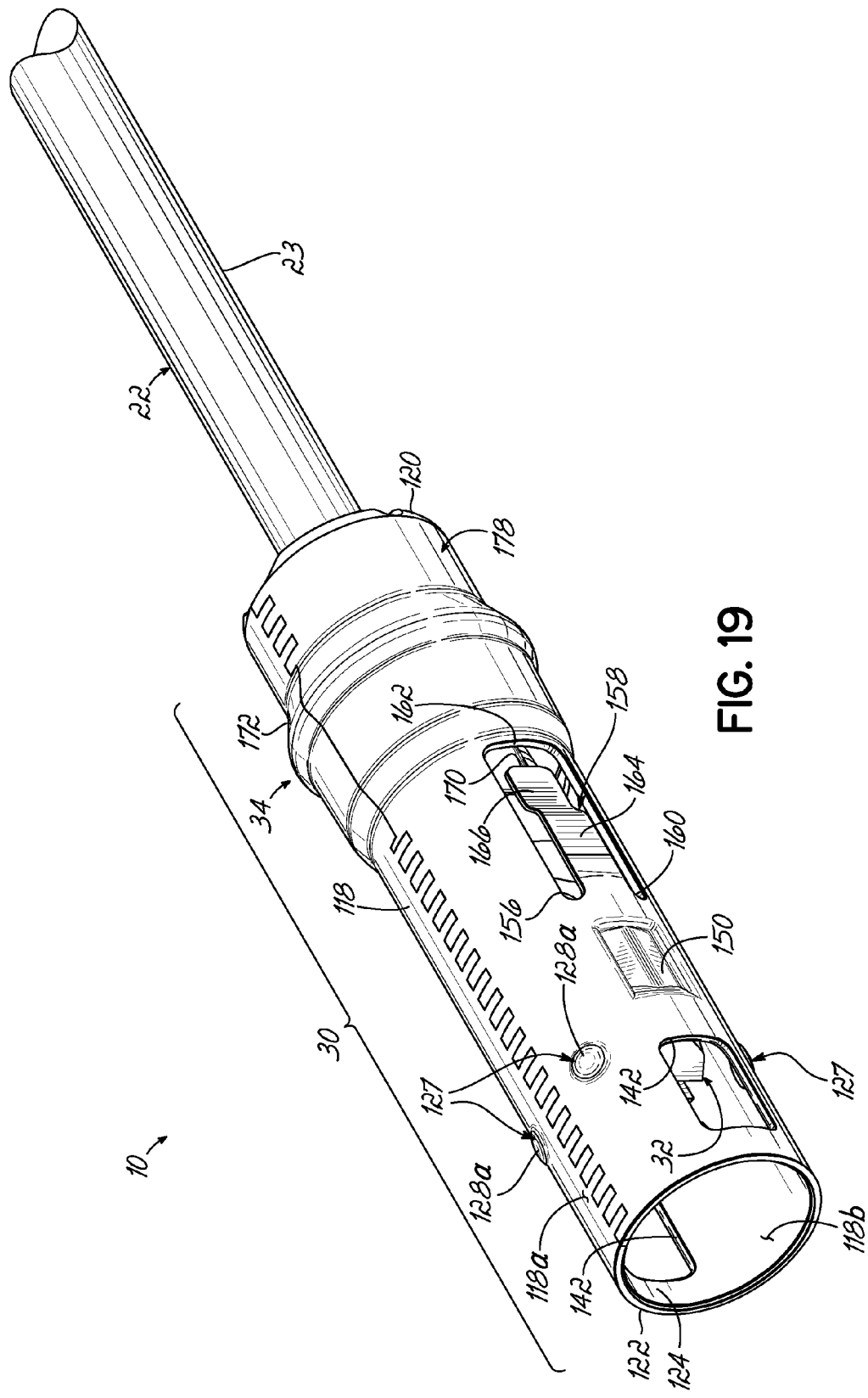
FIG. 19 is a perspective view of the safety catheter in the protected position.

As illustrated in FIGS. 1 and 19, tip protector 30 is of the type configured to enclose the distal portion of the needle cannula 22, including the distal tip 24, while leaving the more proximal portions of the needle shaft 23 exposed. In accordance with one aspect of the invention, the tip protector 30 is a multi-piece design having axially shiftable members that cooperate in a manner to provide shielding of the distal tip 24 of the needle cannula 22, and provide securement of the tip protector 30 to the catheter hub 16 with a generally constant level of holding force. Additionally, as illustrated in FIG. 2, the tip protector 30 may also be of the type configured to be positioned substantially within the catheter hub 16, but as shown herein advantageously has at least a small portion extending proximally outside thereof.

To this end, the tip protector 30 includes a first, inner member 32 received within a second, outer member 34 such that the inner member 32 is axially shiftable relative to the outer member 34 between a first position and a second position, as will be explained in more detail below. In accordance with one aspect of the invention, the inner member 32 may be designed with the primary focus of protecting or shielding the distal tip 24 of the needle cannula 22. This may be achieved, for example, by blocking the path of the needle cannula 22 once the inner member 32 has been axially shifted to the second position. The outer member 34, on the other hand, may be designed with the primary focus of securing and releasing the tip protector 30 to and from the catheter hub 16. While the particular functions of the tip protector 30 may be parsed out to, for example, the inner and outer members 32, 34, it should be recognized that both members 32, 34 are necessary to provide a tip protecting function in the safety catheter 10.

Figure 3:
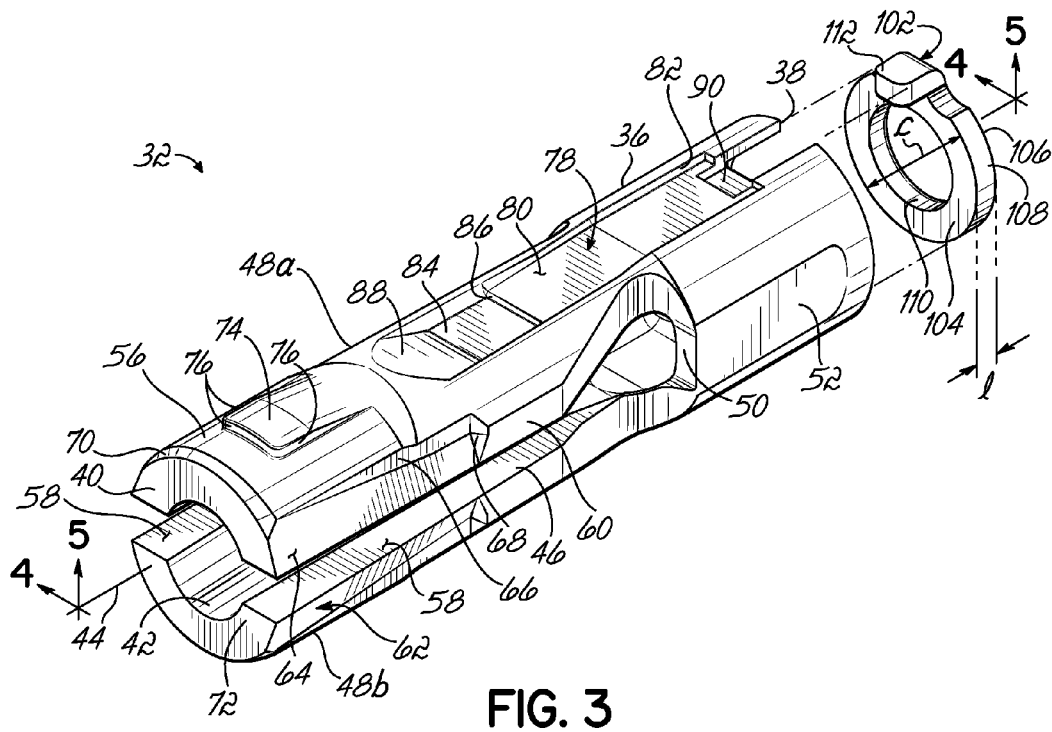
FIG. 3 is a perspective view of the inner member of the tip protector in accordance with one embodiment of the invention.
Figure 4:
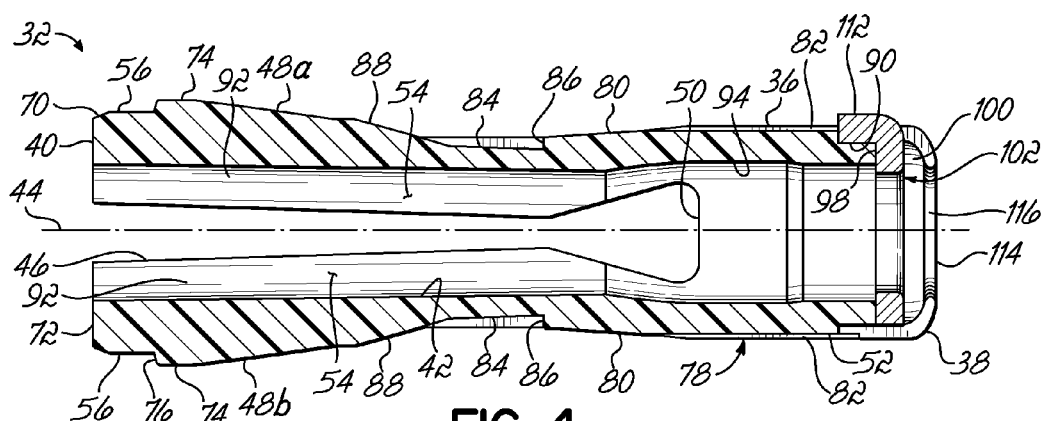
FIG. 4 is a cross-sectional view of the inner member shown in FIG. 3 taken generally along line 4-4 in FIG. 3.
Figure 5:
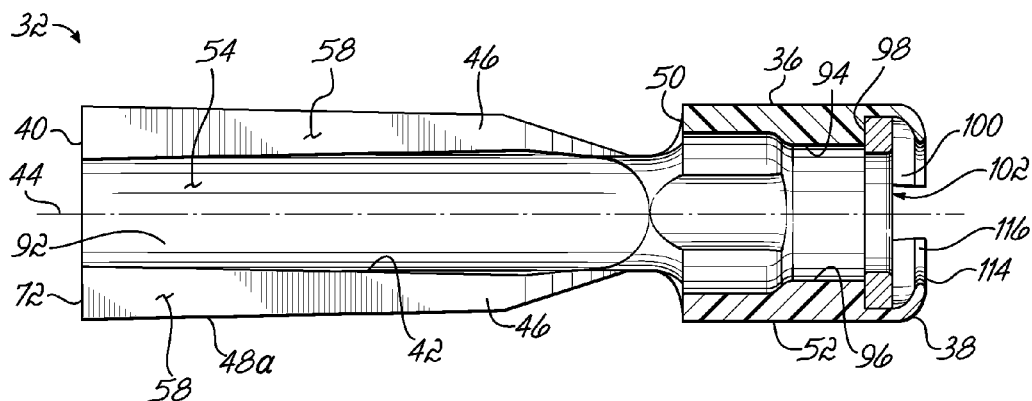
FIG. 5 is a cross-sectional view of the inner member of the tip protector taken generally along line 5-5 in FIG. 3.

In one embodiment, and as illustrated in FIGS. 3-5, the inner member 32 includes a generally cylindrical body member 36 having a proximal end 38, a distal end 40, and a passageway 42 extending between the proximal and distal ends 38, 40. Passageway 42 defines a central axis 44 and is configured to receive at least a portion of the needle cannula 22 therethrough. The cylindrical body member 36 includes a pair of opposed slots 46 formed through the wall of the body member 36 to define a pair of opposed arms 48a, 48b capable of hinging generally inward and outward relative to the central axis 44. In that regard, the slots 46 intersect the distal end 40 of the body member 36 and extend proximally therefrom. The slots 46 have a proximal end 50 that stop short of the proximal end 38 of the body member 36 to define a generally circumferentially continuous base member 52. To facilitate hinging of the arms 48a, 48b, the width of the slots 46 may vary along their length so as to, for example, increase in width adjacent to and in a direction toward the proximal end 50 of the slots 46, as shown in FIGS. 3 and 4, which operates as the hinge or pivot point for arms 48a, 48b.

Figure 20:
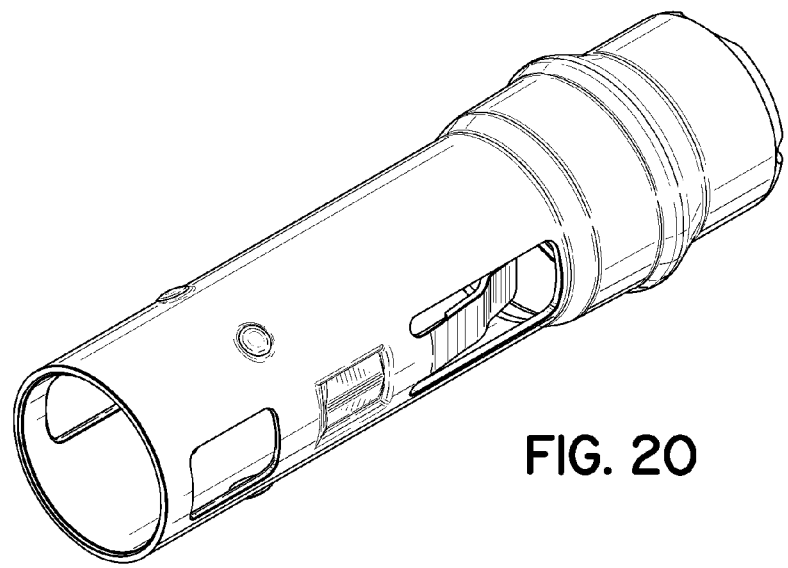
FIGS. 20-24 show various views of one embodiment of the outer member, with FIG. 20 being a perspective view, FIG. 21 being a top view the bottom view being a mirror image thereof, FIG. 22 being a left side view the right side view being a mirror image thereof, FIG. 23 being a proximal end view, and FIG. 24 being a distal end view.
Figure 21:
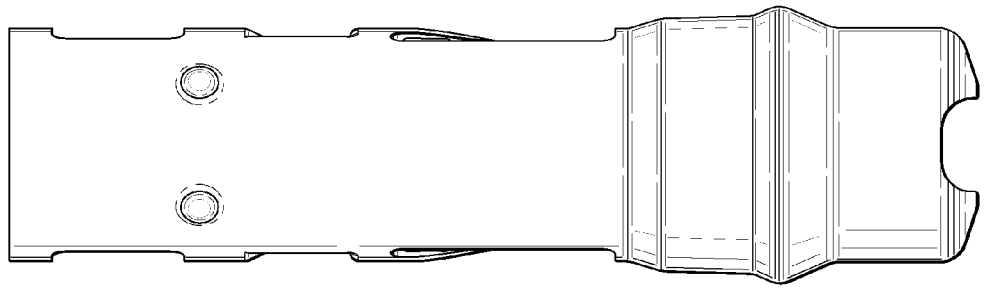
Figure 22:
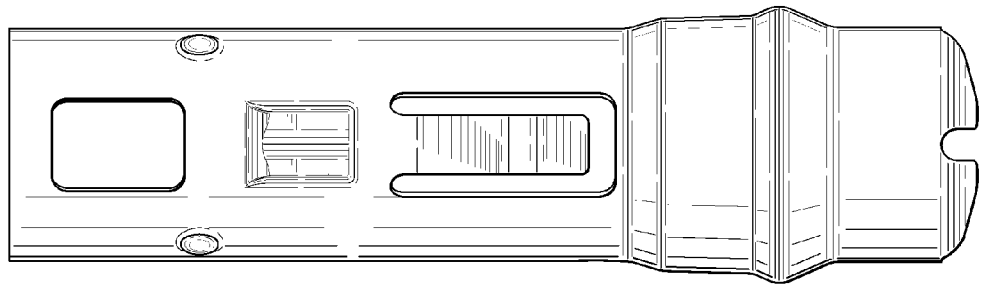
Figure 23:
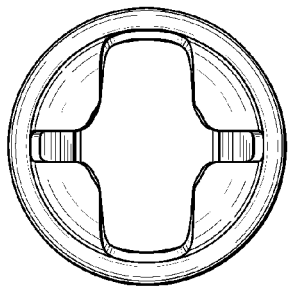
Figure 24:
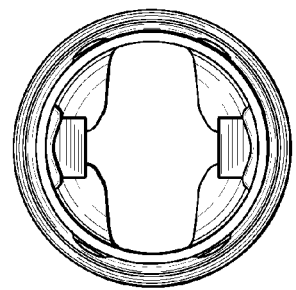
Figure 25:
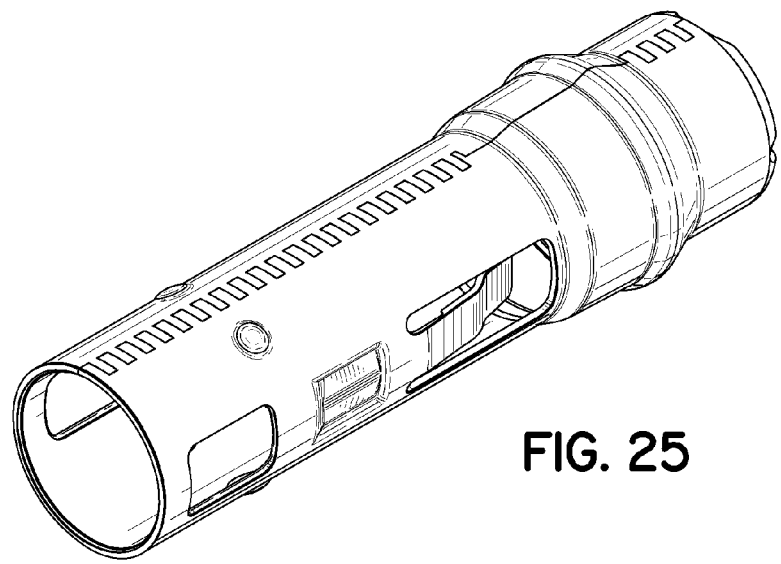
FIGS. 25-30 show various views of an alternative embodiment of the outer member, with FIG. 25 being a perspective view, FIG. 26 being a top view, FIG. 27 being a bottom view, FIG. 28 being a left side view the right side view being a mirror image thereof, FIG. 29 being a proximal end view, and FIG. 30 being a distal end view.
Figure 26:
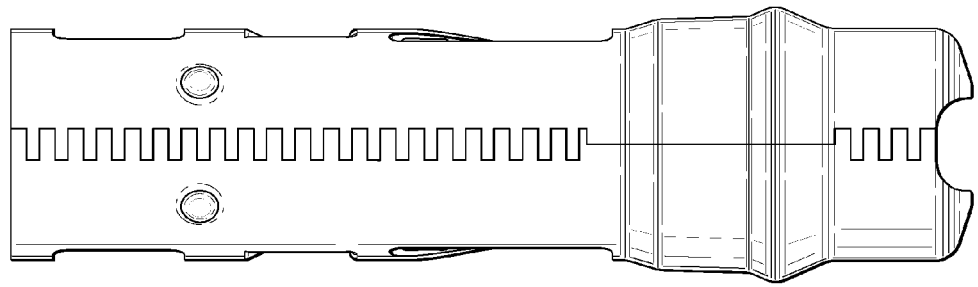
Figure 27:
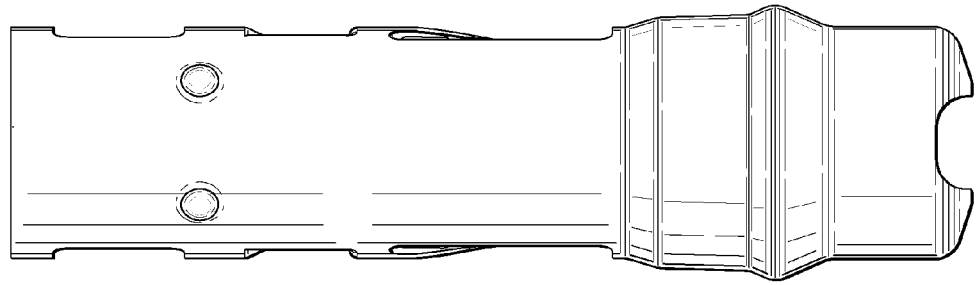
Figure 28:
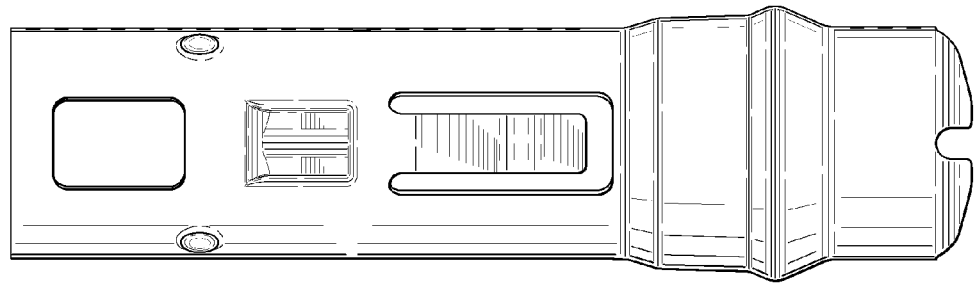
Figure 29:
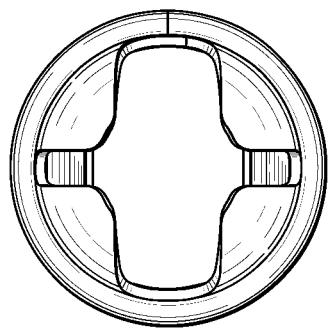
Figure 30:
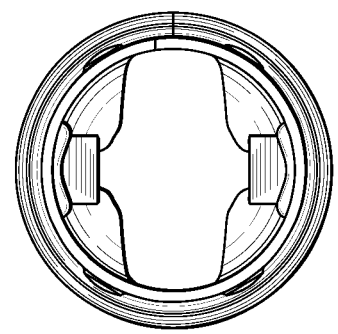
Figure 36:
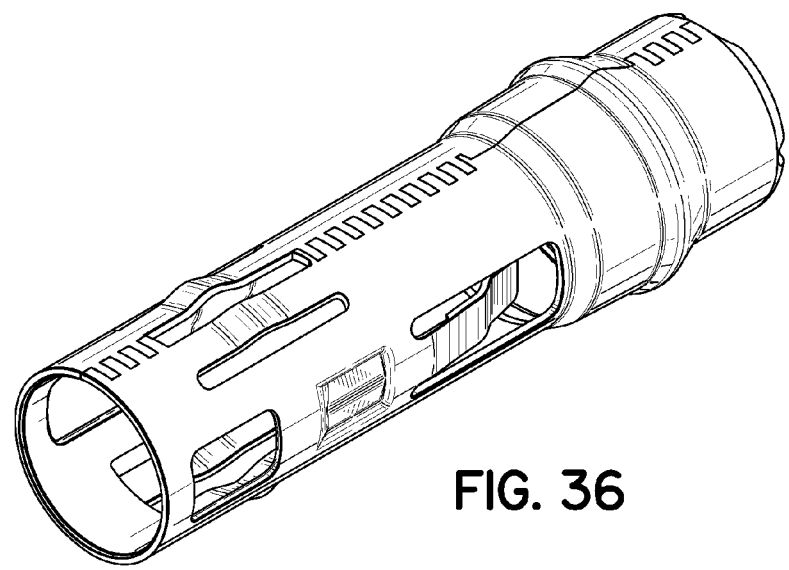
FIGS. 36-41 show various views of an alternative embodiment of the outer member, with FIG. 36 being a perspective view, FIG. 37 being a top view, FIG. 38 being a bottom view, FIG. 39 being a left side view the right side view being a mirror image thereof, FIG. 40 being a proximal end view, and FIG. 41 being a distal end view.
Figure 37:
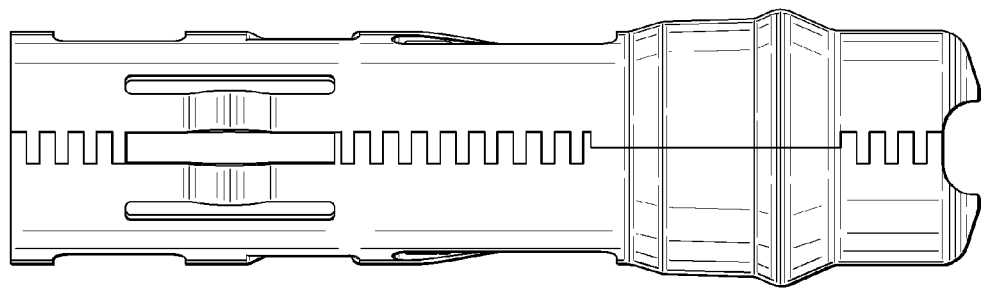
Figure 38:
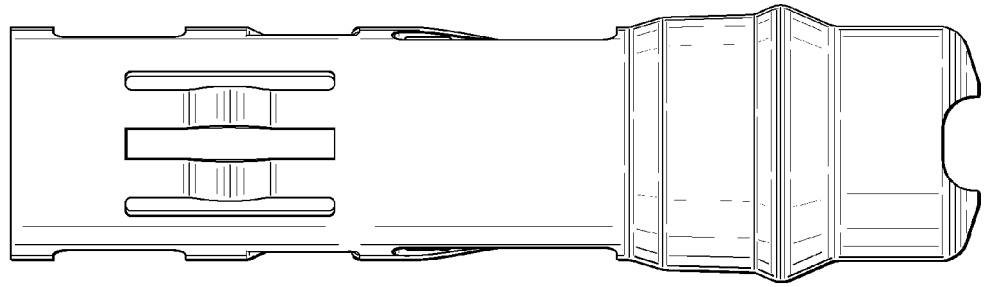
Figure 39:
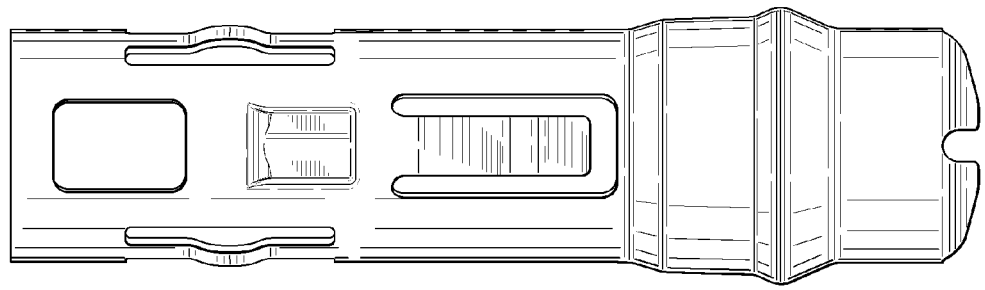
Figure 40:
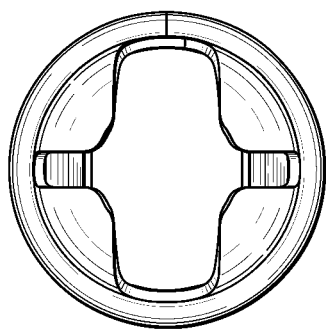
Figure 41:
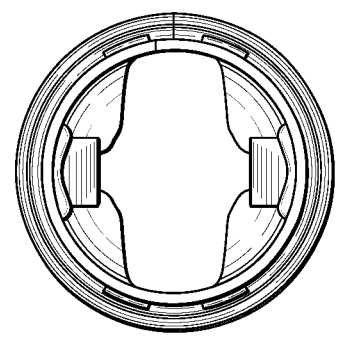

In one embodiment, and although not so limited, the arms 48a, 48b may be essentially mirror images of each other, and thus a description of one of the arms (e.g., arm 48a) will suffice as a description of the other arm (arm 48b). Arm 48a includes an inner surface 54, an outer surface 56, and a pair of slot faces 58 formed by the formation of slots 46 in body member 36. The outer surface 56 may be contoured to facilitate operation of the tip protector 30. To this end, the outer surface 56 may include a first angled surface 60 adjacent each of the slot faces 58 and adjacent the proximal end 50 of the slots 46. A groove 62 may also be formed adjacent each of the slot faces 58 and includes a bottom wall 64, a side wall 66, and a proximal end wall 68 (FIG. 3). The groove 62 extends distally from the first angled surface 60 toward the distal end 40 of the arm 48a and is open along a distal end thereof. Additionally, at least a portion of the distal end 40 of the arm 48a may include a slight chamfer 70 formed in the outer surface 56 thereof which leads to a distal end face 72 of the arm 48a. Although not shown here, the inner surfaces 54 of the arms 48a, 48b may include sidebites extending axially therealong and/or transverse blocking ribs near the distal ends thereof as seen in FIGS. 20 and 21, and the related text at column 22, line 24 to column 23, line 59 of U.S. Pat. No. 8,257,322, those disclosures of which are incorporated herein by reference in their entireties.

As shown in FIGS. 3 and 4, the outer surface 56 of arm 48a may include a raised ridge or boss 74 disposed adjacent the distal end 40 and along an intermediate portion of arm 48a (e.g., generally central of the two grooves 62 and, for example, about ninety degrees offset relative to slots 46). The raised boss 74 defines abutment surfaces 76, the purpose of which is described in more detail below. Moreover, arm 48a may include a second groove 78 formed along an intermediate portion of arm 48a (e.g., generally aligned with raised boss 74) that has a proximal end adjacent the proximal end 38 of body member 36, and a distal end that terminates in arm 48a proximal of raised boss 74. Groove 78 includes a bottom wall 80, and a pair of opposed side walls 82. The groove 78 may have a depth that varies along its length and may further have a cavity 84 formed in the bottom wall 80 thereof. Cavity 84 defines a first end wall 86 and a second end wall 88. In one embodiment, the first end wall 86 may generally form an acute or right angle relative to bottom wall 80, and the second end wall 88 may generally form an obtuse angle relative to the bottom wall 80. In addition to the above, the outer surface 56 of the inner member 32 may include a notch 90 formed adjacent the proximal end 38 and which extends into (e.g., recessed in) the bottom wall 80 of the groove 78.

The inner surface 54 of the inner member 32 may also be contoured to facilitate operation of the tip protector 30. As shown in FIGS. 3 and 5, the inner surface 54 of arm 48a includes a generally smooth distal tapered bore portion 92. In other words, the distal tapered bore portion 92 includes a generally defined radius of curvature that decreases in the distal direction (i.e., toward distal end 40). Collectively, the tapered bore portions 92 of both arms 48a and 48b define a tapered bore that is a portion of passageway 42 which has a first cross dimension at a first proximal location and a second cross dimension at a second distal location that is less than the first cross dimension, at least when the inner member 32 is in its second position relative to outer member 34, as explained in more detail below.

In addition to the above, an inner surface 94 of base member 52 may include an annular rib 96 that generally defines a proximal facing ledge 98. While the embodiment shown in FIGS. 3-5 illustrates a single rib that provides a continuous circumferential ledge, in alternative embodiments, multiple ribs may be utilized to provide a discontinuous ledge (not shown). The ledge 98 generally defines at least in part the boundary of a proximal cavity 100 configured to receive a needle stop member therein. As discussed in more detail below, the stop member may be configured to cooperate with the needle cannula 22 during its withdrawal from the catheter assembly 12 so as to effect relative movement between the needle cannula 22 and the tip protector 30.

In an exemplary embodiment, the stop member may optionally include a stop washer 102 having a distal face 104, a proximal face 106, a side wall 108 extending between the distal and proximal faces 104, 106, and a central aperture 110 also extending between the distal and proximal faces 104, 106 (FIG. 3). The stop washer 102 is generally characterized by the length "l" of the side wall 108 being less than, and preferably significantly less (such as about ⅕ to ½) than a cross-dimension "c" (e.g., diameter or effective diameter) of the distal and proximal faces 104, 106. As also illustrated in FIG. 3, in one embodiment, the stop washer 102 may include at least one leg 112 (one shown) coupled to the side wall 108 and extending distally thereof. While the stop washer 102 is advantageous in many applications, other stop members may be used including, for example, a tubular sleeve. However, a sleeve is axially elongated as compared to a washer and may have certain drawbacks that may not be desirable in certain applications.

When the stop washer 102 is positioned within proximal cavity 100, the distal face 104 thereof is configured to engage the ledge 98 formed by the rib 96. This engagement prevents or limits distal movement of the stop washer 102 relative to the inner member 32. The stop washer 102 may be captured within cavity 100 by suitable formation of the proximal end 38 of the body member 36. To this end, the proximal end 38 includes a proximal end face 114 having an opening 116 formed therein. The opening 116 has a cross dimension (e.g., diameter) that is smaller than a cross dimension of the stop washer 102. Accordingly, the end face 114 operates to prevent or limit proximal movement of the stop washer 102 relative to the inner member 32.

In addition to the above, when the stop washer 102 is disposed within proximal cavity 100, the leg 112 is configured to be received within the notch 90 formed adjacent the proximal end 38 of the body member 36, as illustrated in FIG. 4. The purpose of the leg 112 (and thus the notch 90 that receives leg 112) is primarily directed to facilitating assembly of the safety catheter 10 through an automated manufacturing process. The leg 112 and notch 90 otherwise have no role in the proper functioning of the tip protector 30. Accordingly, those of ordinary skill in the art will realize that the leg 112 and the notch 90 that receives the leg in an assembled condition may be omitted without negatively affecting the operation of the safety catheter 10 depending on the particular requirements or preferences of an assembly process.

The body member 36 of inner member 32 may be formed from suitable materials including various metals and plastics. By way of example, the body member 36 may be formed from such materials as polypropylene, polyethylene, polyoxymethylene (acetal), polycarbonate and nylon. In one aspect, the body member 36 may be formed from plastics or other materials suitable for molding processes including, for example, various injection molding processes. In an exemplary embodiment, the inner member 32 may be formed from plastic through a molding process so as to define the multi-thickness member shown herein. The stop washer 102 may also be formed from suitable materials including various metals and plastics. The stop washer 102 may be generally more rigid than the body member 36 and advantageously may be formed from medical grade stainless steel or other metals. In this regard, the use of a more rigid material at the location of engagement between the needle cannula 22 and the inner member 32 reduces the risk of the plastic inner member from deforming and allowing the needle cannula 22 to be pulled from the tip protector 30.

The stop washer 102 may be assembled with the body member 36 during manufacturing or during a post-manufacturing process of inner member 32. By way of example, the stop washer 102 may be assembled with body member 36 in an over-molding process. In that regard, the stop washer 102 may be suitably located within a mold assembly as an insert. The mold assembly is then closed and the resin that forms the body member 36 is injected into the mold so as to form about the insert. In another embodiment, the body member 36 may be injection molded without the stop washer 102 being assembled therewith. In this method, the proximal end 38 thereof may lack the proximal end face 114 and instead be formed as an open ended tubular extension of cavity 100 (FIG. 3). Subsequent to the molding operation of body member 36, the stop washer 102 may be positioned within the cavity 100 and the proximal end 38 processed to form proximal end face 114. By way of example, a swaging or other similar process may be utilized to form the proximal end face 114. Those of ordinary skill in the art may recognize other processes for manufacturing and/or assembling the inner member 32 and aspects of the invention are not limited to those described herein.

Figure 6:
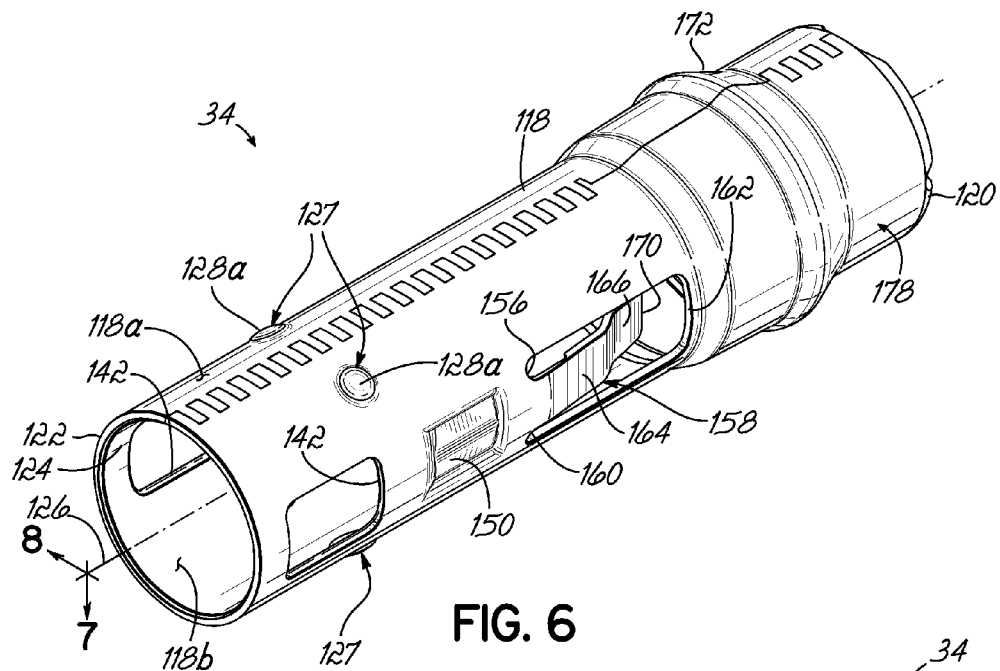
FIG. 6 is a perspective view of the outer member of the tip protector in accordance with one embodiment of the invention.
Figure 7:
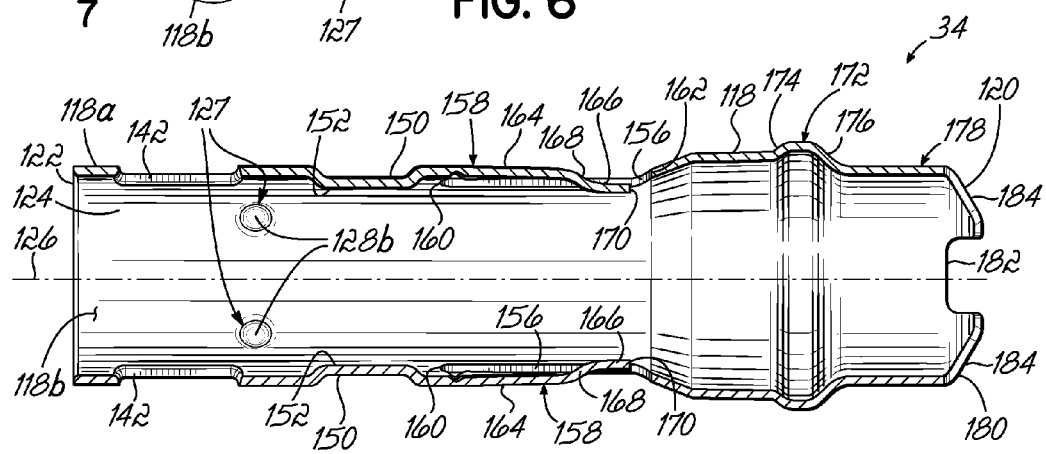
FIG. 7 is a cross-sectional view of the outer member shown in FIG. 6 taken generally along line 7-7 in FIG. 6.
Figure 8:
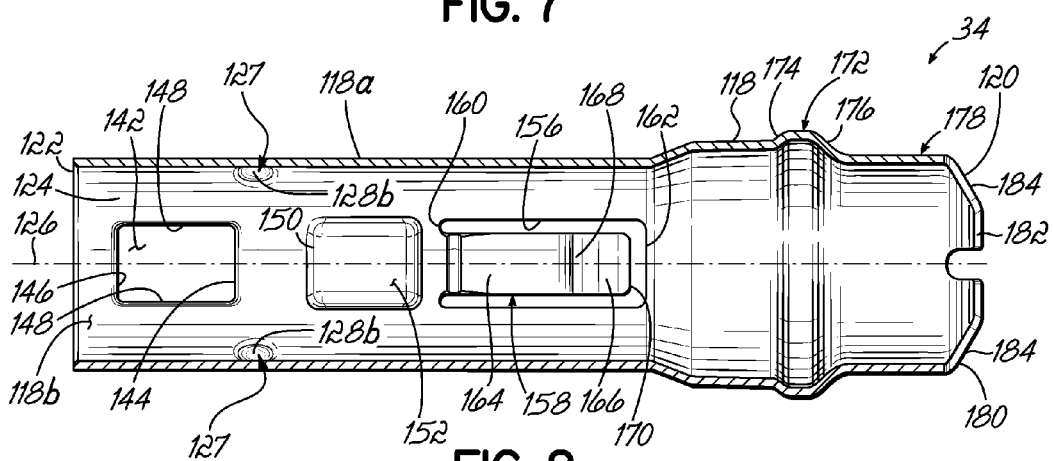
FIG. 8 is a cross-sectional view of the outer member shown in FIG. 6 taken generally along line 8-8 in FIG. 6.

Turning to the outer member 34 illustrated in FIGS. 6-8, the outer member 34 includes a body member 118 which is shown here to be a thin-walled generally cylindrical body member 118 having an outer surface 118a and inner surface 118b. Body member 118 has a proximal end 120, a distal end 122, and a passageway 124 extending between the proximal and distal ends 120, 122. The passageway 124 defines a central axis 126 and is configured to receive at least a portion of the inner member 32 as well as at least a portion of the needle cannula 22. When the inner and outer members 32, 34 are movably coupled in the manner described below, the central axes 44, 126 may be configured to be generally collinear. Outer member 34 includes a number of features that facilitates operation of tip protector 30 through cooperation with the inner member 32 as well as with the catheter hub 16.

Figure 16:
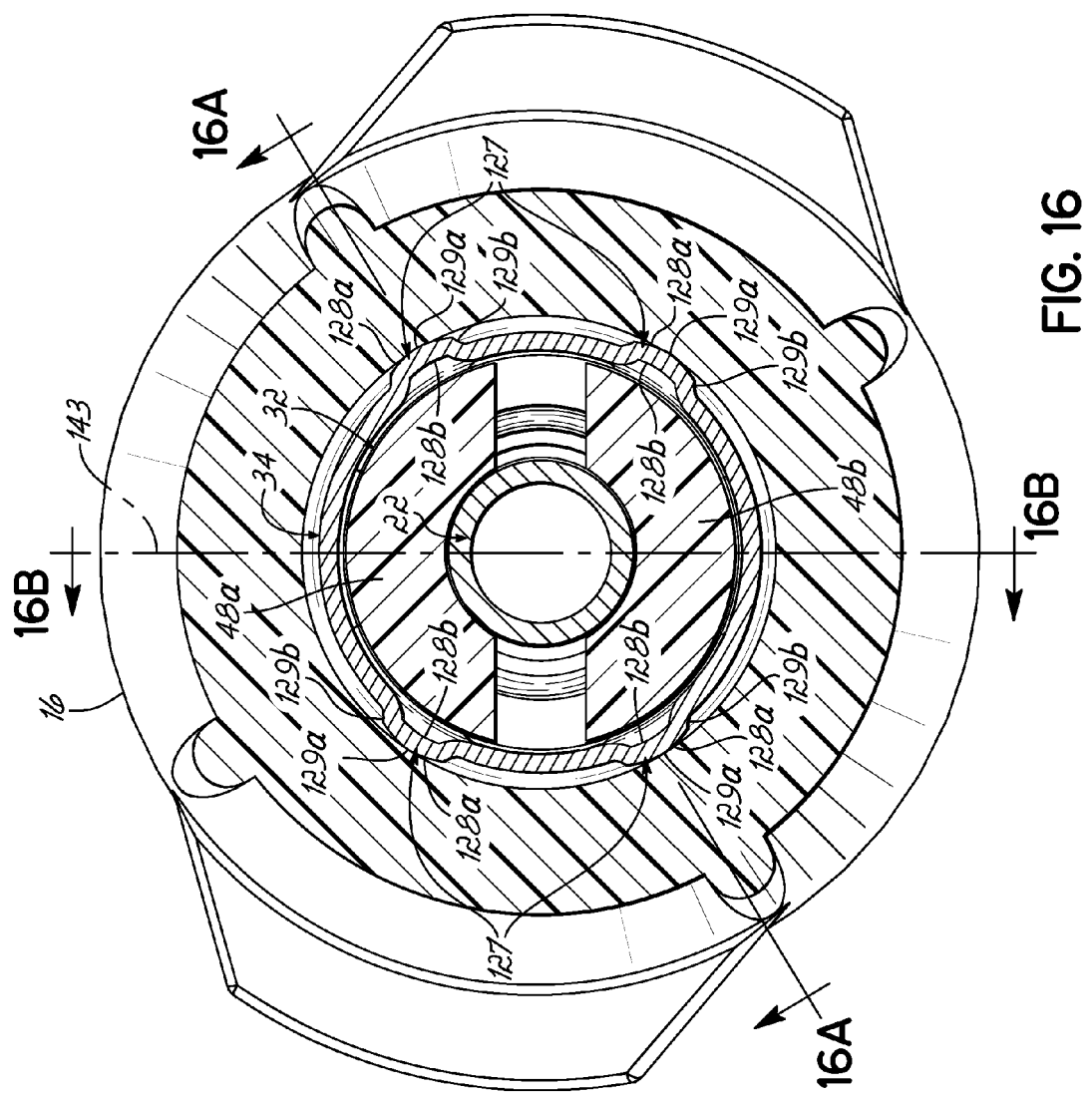
FIG. 16 is a cross-sectional view of the assembly taken along the line 16-16 (shown in FIG. 2) but omitting the details of the needle hub.

In regard to the latter, the generally cylindrical body member 118 includes at least one and preferably a plurality of generally fixed, radially outwardly projecting portions. In one embodiment, with attention to FIGS. 6, 7, and 8, the projecting portions are formed as a plurality of generally round, discrete dimples 127 having an outer surface 128a which defines a radially outermost extent 129a (FIG. 16) and a surface 129b (FIG. 16) extending from outermost extent 129a toward or merging into the outer surface 118a of the body member 118. Surface 129b may advantageously be contoured or sloped. The placement and spacing of the dimples 127 are not limited to the manner shown. For example, the dimples 127 may be offset at different amounts, and some or all of the dimples 127 may be positioned more distally or more proximally than shown. Dimples 127 may also include an inner surface 128b that extends toward or merges into the inner surface 118b of the body member 118. In one embodiment, the outer surface 128a of each dimple is continuous with the outer surface 118a of body member 118. Similarly, the inner surface 128b of each dimple is continuous with the inner surface 118b of the body member 118. As shown, the outer and inner surfaces 128a, 128b of the dimples 127 have a substantially similar contour. Such a configuration may be accomplished through a stamping process, though not so limited. In alternative embodiments, either the outer surface 128a and/or inner surface 128b may not be continuous with the outer and inner surfaces 118a, 118b of the body member 118, respectively. Furthermore, in other embodiments, the outer and inner surfaces 128a, 128b need not have a substantially similar contour. For example, the inner surface 128b may be flat or substantially match the shape of the inner surface 118b of the body member 118 such that the inner surfaces 118b, 128b are relatively indistinguishable.

Figure 6A:
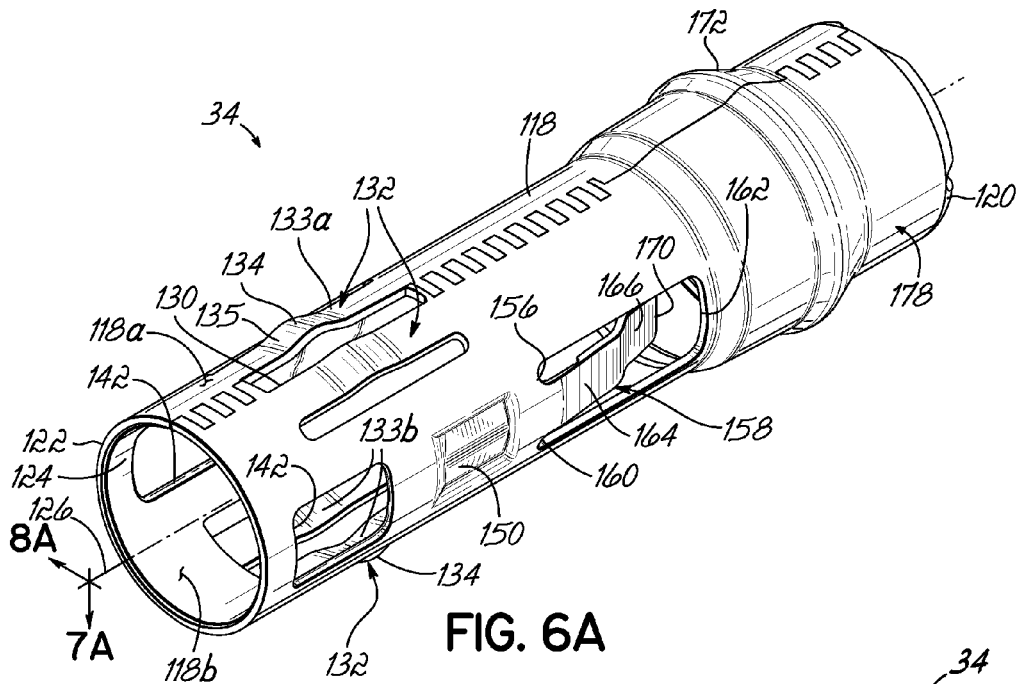
FIG. 6A is a perspective view of the outer member of the tip protector in accordance with one embodiment of the invention.
Figure 7A:
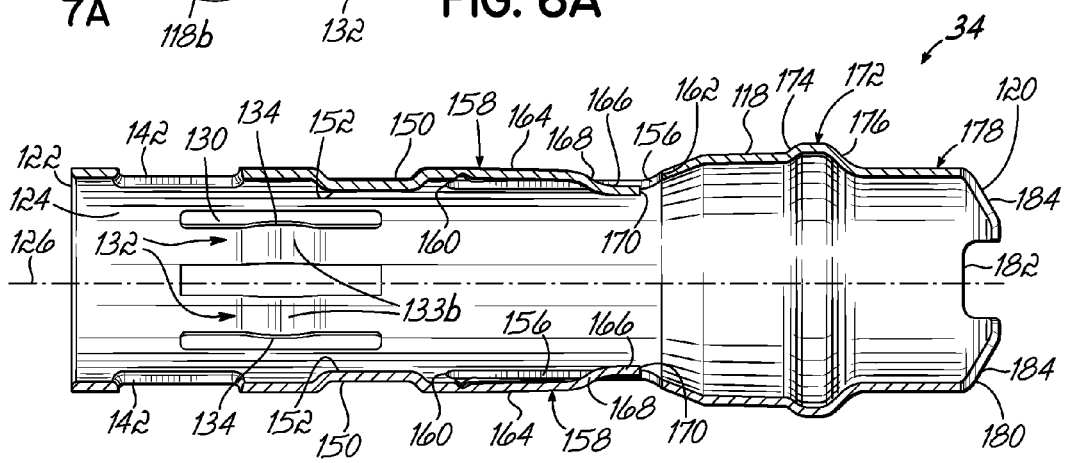
FIG. 7A is a cross-sectional view of the outer member shown in FIG. 6A taken generally along line 7A-7A in FIG. 6A.
Figure 8A:
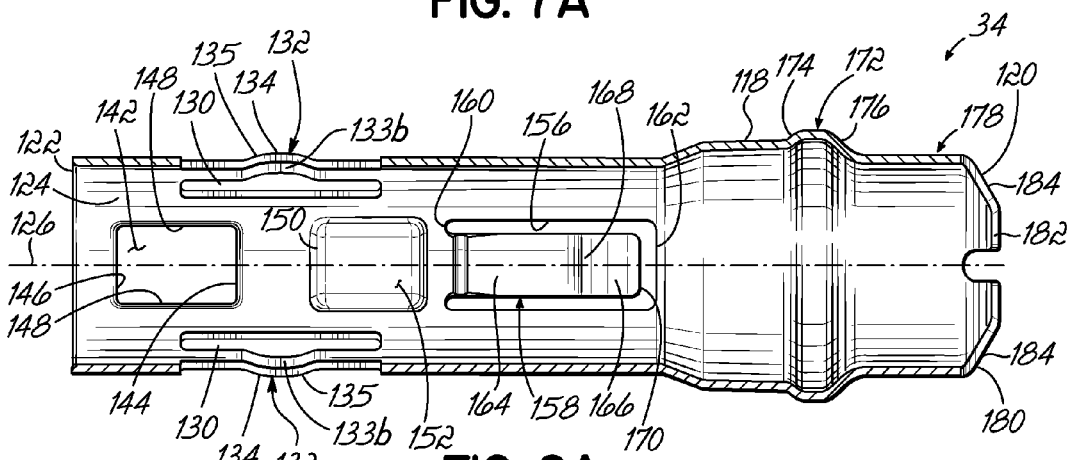
FIG. 8A is a cross-sectional view of the outer member shown in FIG. 6A taken generally along line 8A-8A in FIG. 6A.

Referring to FIGS. 6A, 7A, and 8A, an alternative embodiment of an outer member 34 is shown. Many of the components of this embodiment of the outer member 34 are identical or substantially similar to the components described above with reference to the embodiment shown in FIGS. 6, 7, and 8, and these components have been marked with the same reference numbers in this embodiment without additional explanation below. To this end, generally cylindrical body member 118 may include, additionally or alternatively, a cutout 130 through the body and at least one, but preferably a pair of fixed, rigid struts 132 extending across the cutout 130. The struts 132 extend generally parallel to the central axis 126. As shown, each of the struts 132 has an outer surface 133a which defines a radially outermost extent or portion 134 and a contoured or sloped surface 135 extending from outermost extent 134, at least in the proximal direction and also advantageously in the distal direction. The strut portion 134 and contoured or sloped surface 135 are generally rigid and fixed such that either of them, alone or in combination, defines a generally fixed radially outwardly projecting portion of the outer member 34. Struts 132 also include an inner surface 133b. Inner and outer surfaces 133a and 133b communicate with the outer and inner surfaces 118a, 118b of the body member 118, respectively. In one embodiment, the outer surface 133a of each strut 132 is continuous with the outer surface 118a of body member 118. Similarly, the inner surface 133b of each strut 132 is continuous with the inner surface 118b of the body member 118. As shown, the outer and inner surfaces 133a, 133b of the strut 132 have a substantially similar contour. Such a configuration may be accomplished through a stamping process, though not so limited. In alternative embodiments, the outer surface 133a and/or inner surface 133b may not be continuous with the outer and inner surfaces 118a, 118b of the body member 118, respectively. Furthermore, in other embodiments, the outer and inner surfaces 133a, 133b need not have a substantially similar contour. For example, the inner surface 133b may be flat or substantially match the shape of the inner surface 118b of the body member 118.

In addition to projecting portions, the outer member 34 may include at least one, and preferably a second pair of opposed, generally rectangular openings or cutouts 142 formed through the outer wall of the body member 118 adjacent, but spaced from, the distal end 122 thereof. In one embodiment, the cutouts 142 may be about ninety degrees offset (e.g., about central axis 126) from an imaginary line (not shown) between dimples 127 (or struts 132) above the cutouts 142. Further, the cutouts 142 may be located slightly distally of projecting portions, such as dimples 127 or struts 132, although not so limited. Cutouts 142 define a proximal edge 144, a distal edge 146, and a pair of side edges 148 (FIG. 8). As will be explained in more detail below, the cutouts 142 are configured to receive the raised bosses 74 on the inner member 32 when the safety catheter 10 is in the ready position.

The outer member 34 may further include at least one, and preferably a pair of opposed, generally rectangular indentations 150 formed in the outer wall of the body member 118.

The indentations 150 may be generally axially aligned with cutouts 142 (e.g., about ninety degrees offset from the imaginary line between the dimples 127 (or struts 132) of a pair) and positioned proximally thereof. As can be appreciated, the indentations 150 formed on the outer surface of body member 118 result in projections relative to the inner surface of the body member 118 that defines engaging surfaces 152 that extend away from an inner surface and into the passageway 124 of the outer member 34. The indentations 150, in effect, define a reduced cross dimension portion of passageway 124 and are configured to cooperate with the inner member 32 in a manner to be described in more detail below. A hole (not shown) may be formed in at least one of the indentations 150. Similar to above, the hole plays no role in the functioning of tip protector 30. Instead, the optional hole may facilitate assembly, such as providing a visual aid during the assembly process of the catheter device 10. Again, depending on the particular assembly process, the hole may be omitted without negatively impacting the operation of tip protector 30.

In addition to the above, the outer member 34 may include at least one, and in an exemplary embodiment, a pair of opposed slots 156 in body member 118 which extend in a generally proximal-distal direction and are generally axially aligned with the indentations 150 of outer member 34. The slots 156, however, may be positioned generally proximally of indentations 150. A generally flexible locking tab 158 may be generally disposed in the at least one slot 156, and preferably in each of the slots 156. In that regard, the flexible locking tabs 158 may be coupled to a distal end 160 of the slots 156 and extend proximally, but stop short of the proximal end 162 of slots 156. Each of the flexible locking tabs 158 may include a distal tab portion 164, a proximal tab portion 166, and an intermediate tab portion 168. The distal tab portion 164 may be configured to generally lie within the slot 156 (e.g., within the perimeter of the outer member 34), although not so limited. The intermediate tab portion 168, however, may be generally arcuate so as to define an offset between the distal tab portion 164 and the proximal tab portion 166. In this regard, the proximal tab portion 166 may be positioned generally inward of distal tab portion 164 relative to central axis 126 of outer member 34 so as to project into passageway 124. The proximal tab portion 166 terminates in a contacting edge 170, the purpose of which is to be described in more detail below.

Adjacent the proximal end 120 of outer member 34 is a generally outwardly extending flange 172. In one embodiment, the flange 172 is circumferentially continuous (e.g., annular). In an alternative embodiment, the flange 172 may be circumferentially discontinuous and define one or more flange portions that project generally outwardly from body member 118 (not shown). Flange 172 defines a generally distally-facing lip 174 and a generally proximally-facing lip 176. As discussed in more detail below, the flange 172 may be configured to cooperate with the catheter hub 16 during use. The flange 172 may also be configured to cooperate with the needle hub 20, as discussed below. The proximal end 120 of body member 118 may further include a generally cylindrical extension portion 178 proximal of the flange 172. The extension portion 178 terminates in a generally conical proximal end face 180 having an opening 182 configured to receive at least a portion of the needle cannula 22 therethrough. In one embodiment, the proximal end face 180 may be formed by a plurality of inwardly directed tabs 184 (four shown) that define the opening 182.

The cylindrical body member 118 of outer member 34 may be formed from suitable materials including various metals and plastics. In an advantageous aspect, the body member 118 may include a thin-walled cylinder formed from sheet stock metals capable of being formed into a generally cylindrical member. Such metals include medical grade stainless steels (e.g., 410 stainless steel, 17-7 stainless steel, etc.) with or without heat treatment or other processing to achieve a suitable hardness or other desired characteristics. In an exemplary embodiment, the outer member 34 may be formed through a stamping process of the sheet stock, which stamped material is then put through a rolling process to form the outer member 34. The edges of the rolled material may then be joined through a suitable process including welding, bonding or other process. In one embodiment, the edges may include interlocking features to enhance the securement of the edges to form the cylindrical body (e.g., a zipper configuration). Those of ordinary skill in the art may recognize other processes for forming outer member 34 or for coupling the edges to form a generally cylindrical shape. In contrast to previous designs, the outer member 34 has a thin-walled (but sufficiently strong) design that provides increased space for the inner member 32 (e.g., bulkier, plastic inner member 32).

Figure 9:
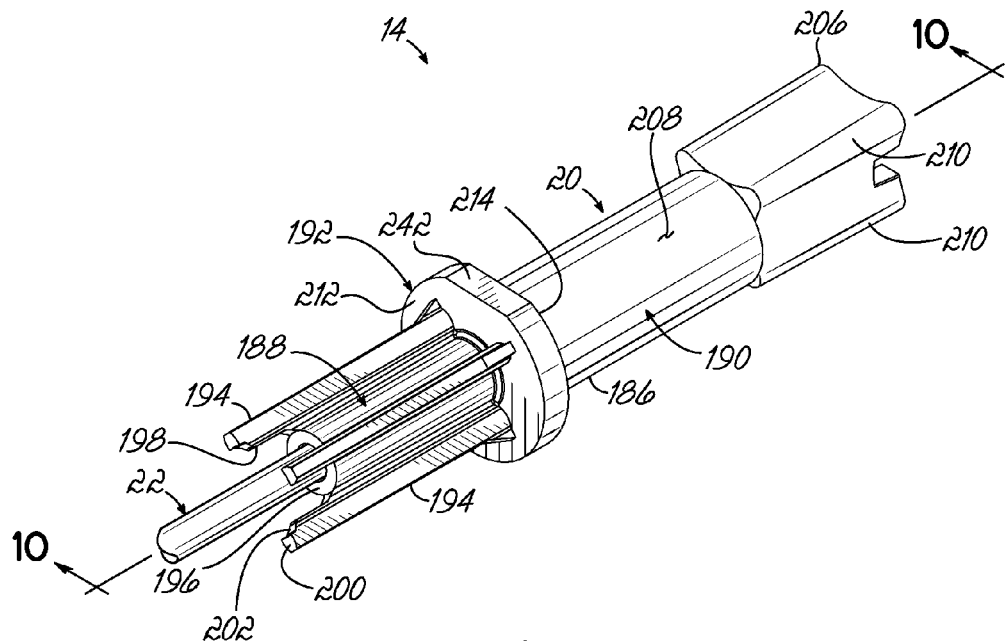
FIG. 9 is a partial perspective view of the needle assembly in accordance with one embodiment of the invention.
Figure 10:
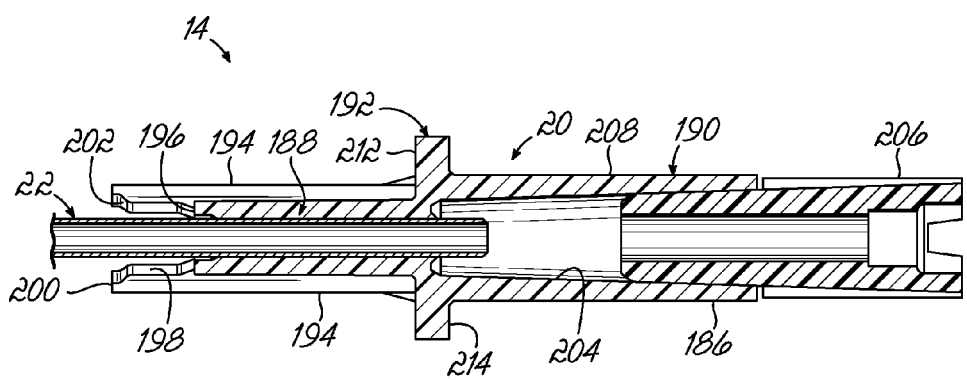
FIG. 10 is a partial cross-sectional view of the needle assembly shown in FIG. 9 taken generally along line 10-10 in FIG. 9.

As described above, the needle assembly 14 generally includes needle hub 20 and needle cannula 22 coupled to a distal portion of needle hub 20 with a needle shaft 23 extending distally thereof. As shown in more detail in FIGS. 9 and 10, the needle hub 20 may include a generally cylindrical body member 186 having a distal nose 188, a proximal tubular portion 190, and a generally outwardly extending intermediate flange 192 disposed therebetween. The distal nose 188 may be configured to receive therein and secure thereto a proximal portion of the needle cannula 22. The distal nose 188 may further include a plurality of circumferentially spaced spines 194 (four shown) that extend in a generally proximal-distal direction therealong. The spines 194 provide increased strength to the needle hub 20 and may further facilitate assembly of the safety catheter 10. At least one, and preferably each of the spines 194 extends beyond a distal end 196 of nose 188 to define an inner surface 198 and a generally distally-directed end face 200. Additionally, a distal end of inner surface 198 may include a taper or bevel 202.

The proximal tubular portion 190 defines an interior chamber 204 that is in fluid communication with a lumen of the needle cannula 22 such that the chamber 204 may operate as a flash chamber for the safety catheter 10, as is generally known in the art. A flash plug 206 closes off the chamber 204 and is configured to allow gases to pass therethrough while retaining liquid, such as blood and other bodily fluids, within chamber 204. In one embodiment, an outer surface 208 of the proximal tubular portion 190 is generally smooth. In an alternative embodiment, however, the outer surface 208 may include grip-enhancement features, such as various depressions or projections that facilitate gripping of the needle hub 20 by a user (not shown). In such a case, the ridges 210 on flash plug 206 may be oriented relative to the proximal tubular portion 190 so as to generally axially align with any such grip-enhancement features.

The intermediate flange 192 may be generally disposed between and extend generally outwardly of the distal nose 188 and the proximal tubular portion 190. In one embodiment, intermediate flange 192 may be generally disc-shaped and include a distal end face 212 and a proximal end face 214. The spines 194 on distal nose 188 may extend from distal end face 212, as shown. In one aspect, the intermediate flange 192 may be configured to cooperate with the sheath 28 that protects the safety catheter 10 during transit and storage. In that regard, the proximal opening 216 in sheath 28 (FIG. 1) may include one or more tabs (not shown) that provide a snap-fit feature between the needle hub 20 and sheath 28. More particularly, when the needle hub 20 is inserted into the sheath 28, the tabs at proximal opening 216 may be configured to engage the proximal end face 214 of intermediate flange 192 to secure the more distal portions of needle assembly 14 (and the catheter assembly 12 as well) within the sheath 28.

Figure 11:
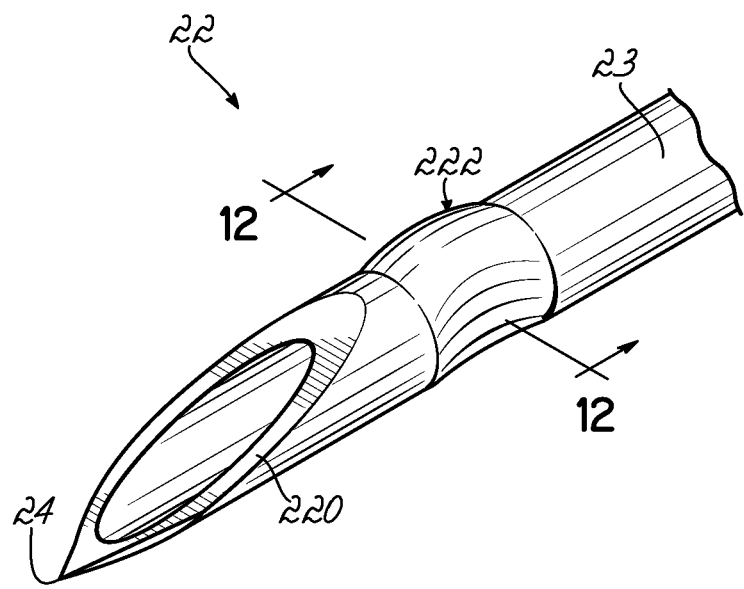
FIG. 11 is a partial perspective view of the needle cannula showing an engaging feature in accordance with one embodiment of the invention.
Figure 12:
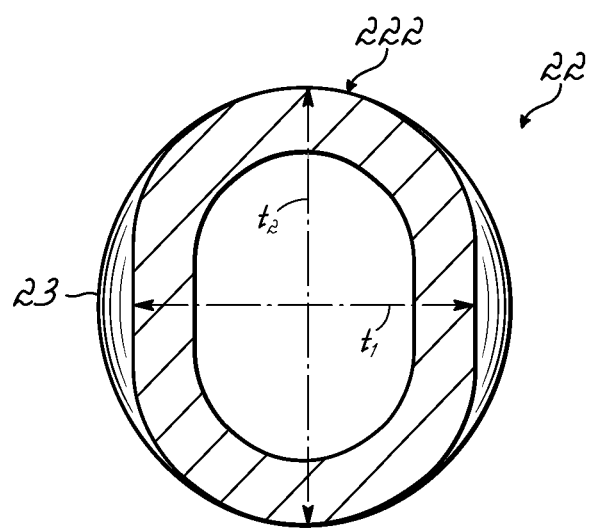
FIG. 12 is a cross-sectional view of the needle cannula shown in FIG. 11 taken generally along line 12-12 in FIG. 11.

As shown in these figures, the needle cannula 22 includes a generally straight, cylindrical and smooth needle shaft 23, a distal portion of which includes a bevel 220 that defines distal tip 24 to be sharp. The needle cannula 22 may be formed from suitable medical grade materials, such as stainless steel or other suitable materials, and the bevel 220/distal tip 24 may be formed in needle shaft 23 through conventional processes generally known in the art. However, as best illustrated in FIGS. 1, 11, and 12, the needle cannula 22 may include an engagement feature adjacent a distal end thereof configured to cooperate with the inner member 32 to axially shift the inner member 32 from the first position to the second position relative to the outer member 34, as discussed below. In one exemplary embodiment, the engagement feature includes a protuberance 222 adjacent a distal end of the needle cannula 22 and proximal of bevel 220.

For reasons that will become clearer below, the protuberance 222 defines a cross dimension that is greater than a cross dimension of the needle shaft 23 proximal of the protuberance 222. In one embodiment, the protuberance 222 may be formed through a pressing or pinching process. To this end, opposed pressing members (not shown) may press against the needle shaft 23 so as to generally decrease a cross dimension thereof in a first transverse direction $t_1$. As illustrated in FIG. 12, the pressing of the needle shaft 23 in the first transverse direction $t_1$ causes a corresponding bulge or increase in a cross dimension of the needle shaft 23 in a second transverse direction $t_2$, which may, for example, be about ninety degrees offset from the first transverse dimension $t_1$. The pressing process described above is only one exemplary method for forming the protuberance 222 on needle cannula 22. Those of ordinary skill in the art may recognize other processes that result in a protuberance 222 having a cross dimension that is greater than a cross dimension of the needle shaft 23 proximal thereof. The engagement feature may be integrally formed with needle cannula 22 (such as described above) or may be formed by fixing a separate element to the needle shaft 23. For example, a ring member (not shown) may be welded, bonded or otherwise secured to needle shaft 23 to form protuberance 222.

Figure 13:
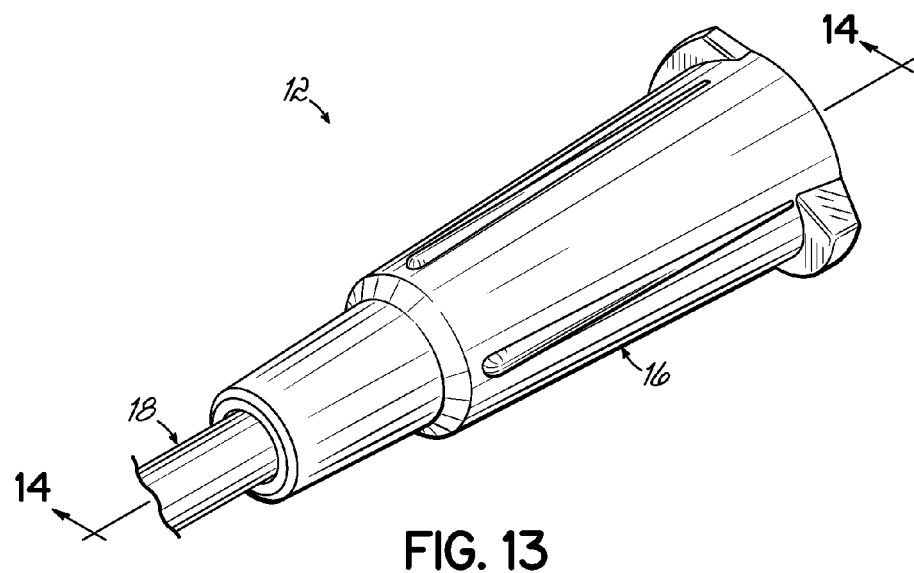
FIG. 13 is a partial perspective view of the catheter assembly in accordance with one embodiment of the invention.
Figure 14:
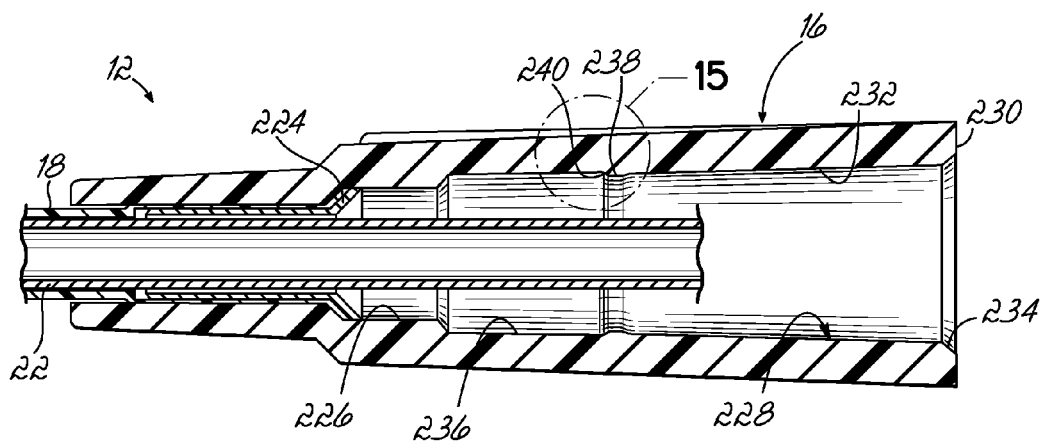
FIG. 14 is a partial cross-sectional view of the catheter assembly shown in FIG. 13 taken generally along line 14-14 in FIG. 13.
Figure 15:
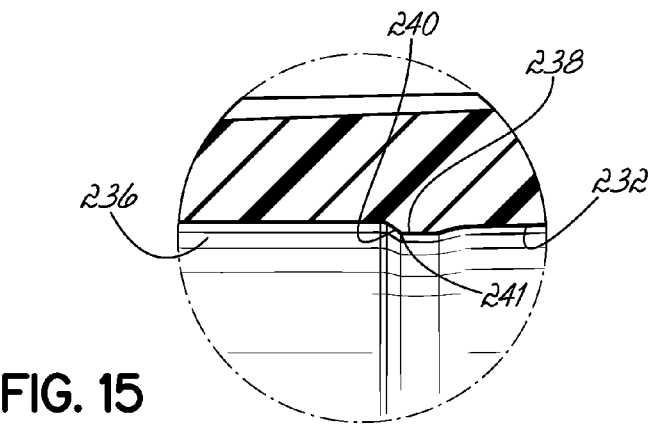
FIG. 15 is an enlarged view of the encircled portion shown in FIG. 14.

As shown in more detail in FIGS. 13-15, the catheter assembly 12 includes a catheter hub 16 and a catheter tube 18 coupled to a distal portion of catheter hub 16 and extending distally thereof. For example, as is generally known in the art, the proximal end of the catheter tube 18 may be coupled to a metal eyelet 224, which eyelet 224 is then press fit within a distal cavity 226 of the catheter hub 16. The catheter hub 16 defines a proximal cavity 228 open to the proximal end 230 thereof and having a first proximal portion 232 which may be shaped according to Luer taper standards. The first proximal portion 232 may include a bevel or chamfer 234 immediately adjacent proximal end 230. In one embodiment, the proximal cavity 228 may include a second proximal portion 236 having a generally constant cross dimension that is generally greater than (e.g., increased inner diameter) a cross dimension of the first proximal portion 232 adjacent the second proximal portion 236. The second proximal portion 236 may be defined at least in part by a transition region 238, as illustrated in FIG. 15.

As best shown in FIGS. 14 and 15, the transition region 238 defines a retention feature for releasably securing the tip protector 30 to the catheter hub 16. In one embodiment, the retention feature defines a generally outwardly extending retention groove 240 formed therein and may be circumferentially continuous (e.g., an annular groove). In an alternative embodiment, however, the groove 240 may be circumferentially discontinuous (e.g., circumferential groove segments). In still a further embodiment, the proximal cavity 228 may include a single proximal portion 232 that tapers or is otherwise shaped (according to any applicable standards) in a continuous manner from the proximal end 230 (or the end of chamfer 234) to the distal cavity 226 (e.g., no second proximal portion 236 or transition region 238) wherein the retention groove 240 is formed within the side wall of the single proximal portion 232 (not shown). Still further, the retention feature in the catheter hub 16 may have other configurations, including, for example, a circumferentially continuous or discontinuous generally inwardly extending retention rib (not shown). It will be seen, however, that a proximal edge 241 is defined which interacts with the generally fixed radial projections (i.e., dimples 127 or aspects of the struts 132) to provide a holding force between the tip protector 30 and the catheter hub 16.

With each of the elements of the safety catheter 10 described above, assembly of the safety catheter 10 will now be described in more detail. In the initial processing steps, the needle assembly 14 and catheter assembly 12 may be formed using methodologies generally known in the art. To that end, and as explained above, the proximal end of the needle cannula 22 may be press fit or otherwise coupled with the distal nose 188 of the needle hub 20, and the proximal end of the catheter tube 18 may be secured to eyelet 224, and the eyelet 224 secured within the distal cavity 226 of the catheter hub 16. The flash plug 206 may also be inserted into the proximal end of proximal tubular portion 190 of needle hub 20 so as to close off the interior chamber 204. It should be noted that as initially assembled, the needle cannula 22 does not have protuberance 222 or other engagement feature formed therein or coupled thereto.

In some applications, it may be desirable to orient the needle cannula 22 and needle hub 20 in a specific manner. By way of example, to facilitate insertion of the catheter assembly 12 into a vein or artery of a patient, the bevel 220 that defines at least in part the distal tip 24 to be sharp is generally placed in a face-up position, as illustrated in FIG. 1. In some instances, clinicians may find it difficult to orient the bevel 220 in the face-up position by visual inspection of the distal portion of the needle cannula 22. To avoid such a difficulty, the needle hub 20 may be provided with an indicator that indicates the orientation of the bevel 220 relative to the needle hub 20. In one embodiment, for example, the indicator may include a flat 242 formed on the intermediate flange 192 of the needle hub 20 that is generally axially aligned with the bevel 220 in needle cannula 22. In this way, a clinician only has to identify the flat 242 on the needle hub 20 to know the orientation of the bevel 220. It should be recognized that other indicia, including various numbers, letters, symbols, etc., may be provided as an indicator, and the invention is not limited to the flat 242 shown and described herein.

With respect to assembly of the tip protector 30, the inner and outer members 32, 34 may be formed separately and in a manner as described more fully above. Additionally, the stop washer 102 may be coupled to the inner member 32 in a manner as described above. Next, the inner member 32 may be loaded into the outer member 34 by inserting the proximal end 38 of the inner member 32 into the passageway 124 of the outer member 34 via its distal end 122. In one aspect, the inner and outer members 32, 34 may be oriented during this loading process. In that regard, the inner and outer members 32, 34 may be oriented such that the cutouts 142, indentations 150 and flexible tabs 158 of the outer member 34 generally axially align with the raised bosses 74 and grooves 78 formed on the inner member 32. Such orienting of the inner and outer members 32, 34 is generally shown in FIG. 1.

The inner member 32 may be axially received into the outer member 34, such as by being inserted, proximal end 38 first, through the distal end 122 of the outer member 34. Advantageously, inner member 32 is inserted far enough for the proximal end 38 to be adjacent, but spaced from, the proximal end 120 of the outer member 34. In this regard, the inner member 32 may be partially seated within the outer member 34 and subsequently fully seated within the outer member 34. For example, in an automated assembly, it may be desirable to define a pre-assembly position wherein the inner member 32 is partially seated within the outer member 34 (e.g., during movement of the pre-assembled tip protector along the assembly line) and fully seated within the outer member in a separate assembly step. Alternatively, the inner member 32 may be fully seated within the outer member 34 without having a pre-assembly position. In any event, in this embodiment, the inner member 32 is configured to be substantially completely within the outer member 34. As noted below in an alternative embodiment, the invention is not so limited. It will be seen, however, that once assembled, the inner member 32 is axially shiftable relative to the outer member 34.

With the tip protector 30 assembled, the tip protector 30 may be threaded onto the needle cannula 22 by inserting the distal tip 24 thereof into the proximal end of tip protector 30 and more particularly through the proximal openings 182, 116 of the outer and inner members 34, 32, respectively. The various flexible parts of the inner and outer members 32, 34 (e.g., arms 48a, 48b, locking tabs 158, etc.) are not being unduly constrained, such as by the outer member 34 or catheter hub 16, and therefore tip protector 30 may accommodate the insertion of the needle cannula 22 therethrough. The tip protector 30 is located on needle shaft 23 generally spaced from the distal tip 24 thereof so as to provide sufficient space for the formation of the engagement feature, such as protuberance 222. To this end, the protuberance 222 may be formed by a pressing method or other suitable methods as described above.

The catheter assembly 12 may then be loaded onto the needle assembly 14 such that the tip protector 30 is substantially positioned within the catheter hub 16, and the needle hub 20 is in proximity to the proximal end 230 thereof. In that regard, the tip protector 30 will have to be inserted at a force sufficient to overcome the drag forces between the outer member 34 and the catheter hub 16 as well as the force required for the projecting portions to traverse, and eventually be received by, the retention groove 240. In one embodiment, the projecting portion, such as dimples 127 or struts 132, may be configured such that the projecting portion makes contact with the inner wall 244 of the catheter hub 16 when in the ready position. Alternatively, however, the projecting portion may be configured such that it is positioned in the retention groove 240, but spaced from the inner wall 244 of the catheter hub 16. In such an embodiment, should the tip protector 30 be moved proximally away from the catheter hub 16 (i.e., should the tip protector 30 be prematurely pulled out of the catheter hub 16), the projecting portion would contact the wall of the retention groove 240 and restrict further proximal movement.

After being assembled, the assembly is then loaded into the sheath 28 via its proximal opening 216 and secured together in the manner described above. The safety catheter 10 may then be further processed and appropriately packaged in a manner generally known in the art. In one embodiment and as noted above, the assembly process described above may be an automated type of process. The invention is not so limited, however, as manual or hybrid types of processes may be used for assembly of the safety catheter 10.

FIG. 2 illustrates the catheter device 10 in a ready position wherein the bevel 220 and distal tip 24 of the needle cannula 22 extend beyond the distal end 26 of the catheter tube 18, and the safety catheter 10 is ready for insertion into the vasculature of a patient. In the ready position, it will be seen that the inner member 32 is in a distal position relative to the outer member 34. The interaction of the various components of safety catheter 10 when in the ready position will now be described in reference to FIGS. 16A and 16B. When in the ready position, a substantial portion of tip protector 30 is positioned within the catheter hub 16. Specifically, in one embodiment, the inner member 32 is positioned in the catheter hub 16 at least when in the ready position. In that regard, the tip protector 30 is inserted into the catheter hub 16 during assembly until the distal facing lip 174 of flange 172 engages the chamfer 234 adjacent the proximal end 230 of the catheter hub 16. This engagement prevents the tip protector 30 from moving any further distally within the catheter hub 16. In one embodiment, no portion of the tip protector 30, and more particularly, no portion of outer member 34 thereof engages the proximal end 230 of catheter hub 16. In alternative embodiments, however, the tip protector 30 may additionally or alternatively engage the proximal end 230 of catheter hub 16 (not shown). As shown in these figures, a portion of flange 172 and extension portion 178 may project beyond the proximal end 230 of catheter hub 16. The length $l_1$ of the tip protector 30 that extends proximal of the proximal end 230 is generally too small to be gripped or manipulated by the human hand. Indeed, that portion of the outer member 34 that projects out of the catheter hub 16 is covered by the spines 194 and therefore could not be grasped in any event.

Figure 16A:
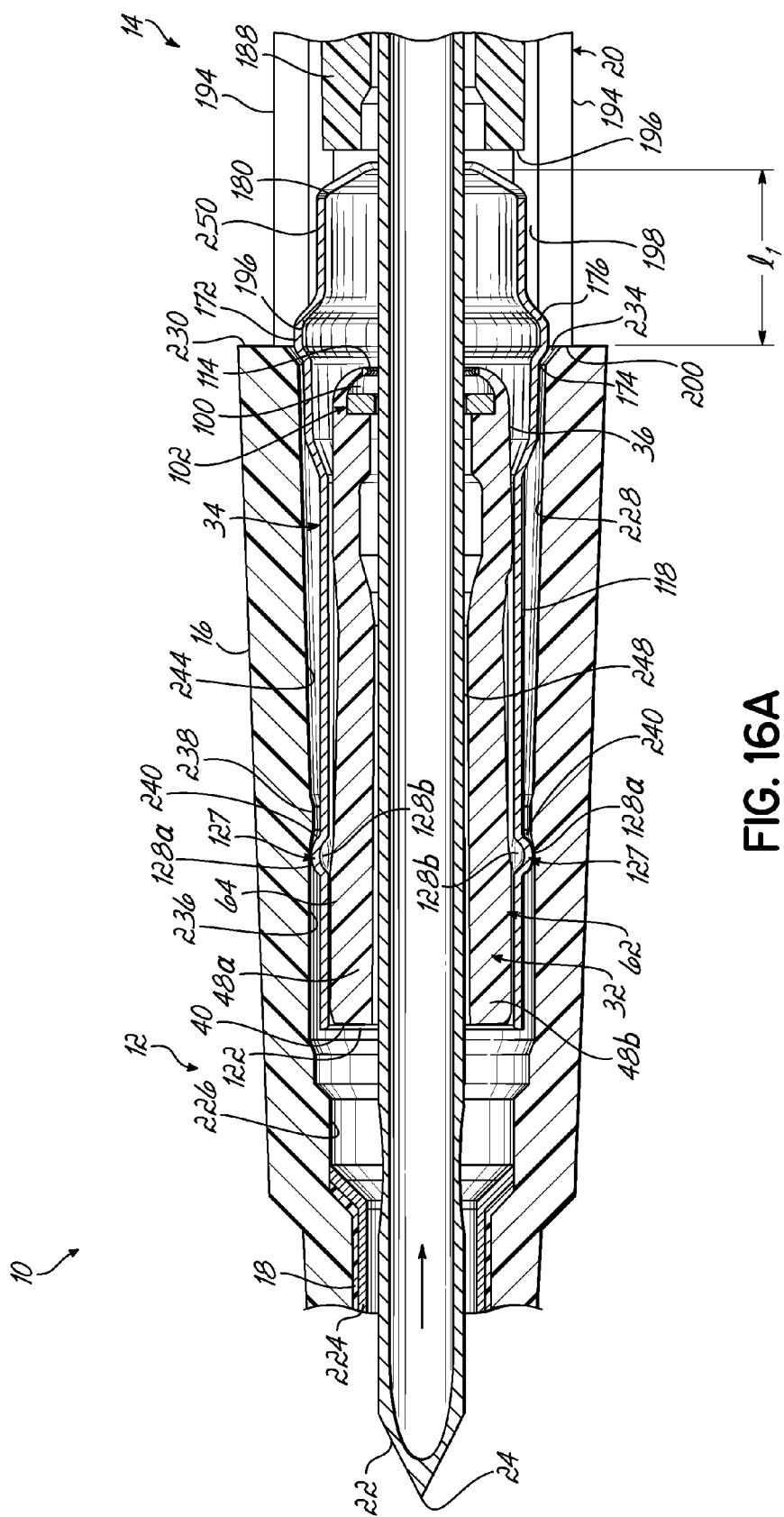
FIG. 16A is a partial cross-sectional view, taken along line 16A-16A (shown in FIG. 16) of the safety catheter in the ready position, wherein the inner member is in a first position relative to the outer member.

The tip protector 30 is secured within the catheter hub 16 through an interaction between the outer member 34 and the inner wall 244 of the catheter hub 16. More particularly, and as best illustrated in FIG. 16A, when in the ready position, dimples 127 are received in the retention groove 240 such that the outer member 34, and thus the tip protector 30, is prevented from moving in the proximal direction, unless the outer member 34 is subjected to a substantial amount of force in the proximal direction, as described below. Outer member 34, dimples 127, and catheter hub 16 may be sized such that there is essentially an interference fit between the dimples 127 and retention groove 240 of the catheter hub 16. This interference fit between dimples 127 and retention groove (and potentially also between dimples 127 and inner wall 244, as described above), and particularly, the interaction of the proximal edge 241 and the dimples 127, provides a holding force between the outer member 34 and the catheter hub 16 that remains constant irrespective of the position of the inner member 32 between first and second positions (such as between the distal position and a proximal position relative to the outer member 34 as described below). The dimples 127 are received in the retention groove 240 and may not be removed or disengaged from the catheter hub 16 without overcoming the holding force during a proximal movement of the tip protector 30. In the alternative embodiment wherein the projecting portions are defined by the struts 132, the strut portions 134 and/or contoured slope surface 135 thereof interact with the retention groove 240 in inner wall 244 in a substantially similar manner as described with respect to the dimples 127.

In this regard and in an exemplary embodiment, the outermost extent 129a of dimples 127 or the strut portions 134 extend radially outward of the outer surface 118a of the outer member 34 by an amount between about 0.05 mm and about 0.15 mm. The retention groove 240 may have a height (e.g., as measured from the inner wall 244 at the retention groove 240 to the most radially-inward aspect of the inner wall 244 just proximally adjacent the retention groove 240) between about 0.09 mm and about 0.18 mm. The dimensional relationship between these two is configured to provide a substantially constant holding force of the tip protector 30 to the catheter hub 16, especially upon interaction between proximal edge 241 and either dimples 27 or struts 132 of between about 0.10 pounds and about 0.50 pounds. As will become clear, due to the fixed nature of the projecting portion on the outer member 34, this holding force is independent of the position of the inner member relative to the outer member 34.

Figure 16B:
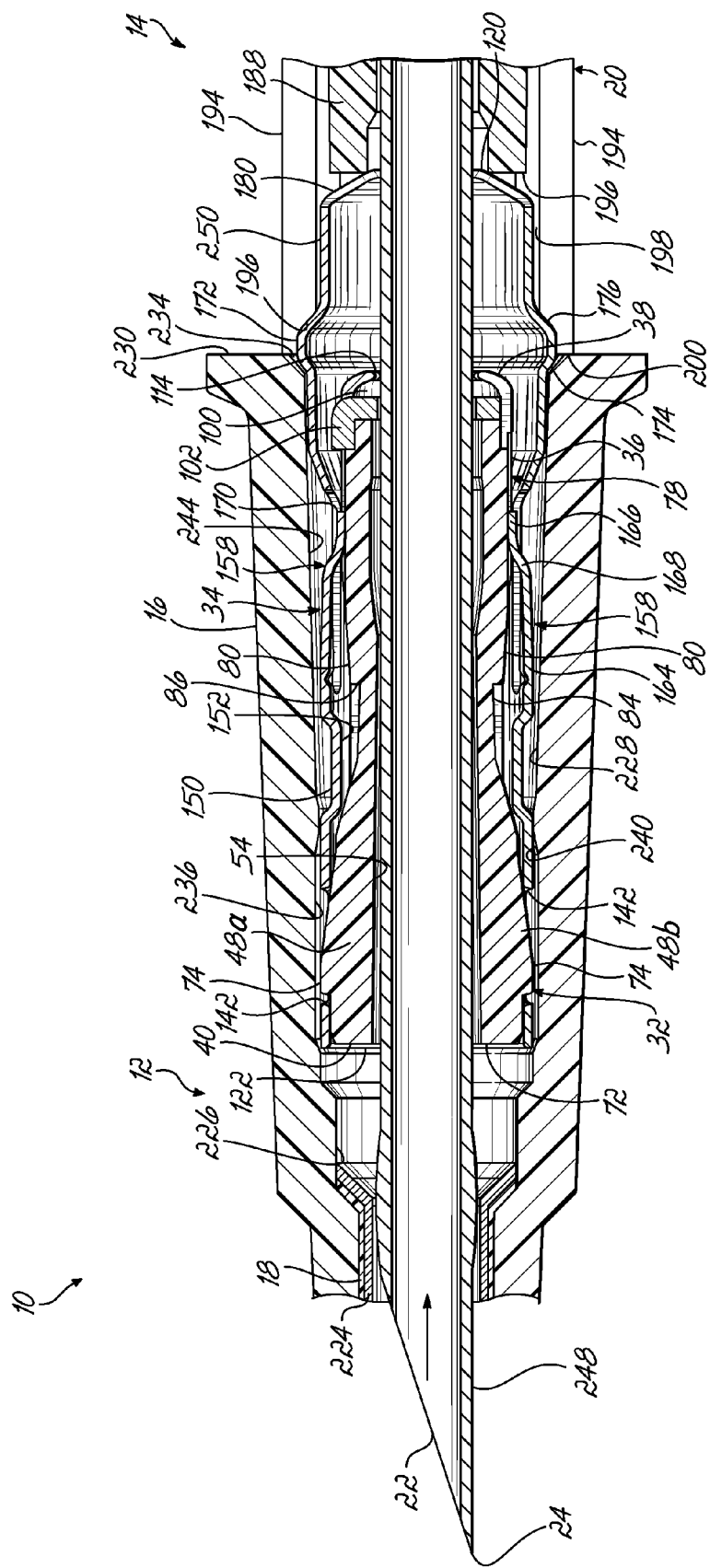
FIG. 16B is another partial cross-sectional view of the safety catheter in the ready position, taken along line 16B-16B (shown in FIG. 16.)

As further illustrated in FIGS. 16A and 16B, when in the ready position, the inner member 32 is in its first or distal position relative to outer member 34 and is entirely positioned within the outer member 34. In one embodiment, the arms 48a, 48b may be configured to be biased generally radially outward relative to central axis 44. For example, the outer member 34 may be configured to constrain the arms 48a, 48b (i.e., but for the outer member 34, the arms 48a, 48b would move further apart from one another). When in the ready position, the inner surface 54 of the arms 48a, 48b may be in proximity to an outer surface 248 of the needle shaft 23. For example, in one embodiment, the inner surface 54 of arms 48a, 48b may be slightly spaced from the outer surface 248 of the needle shaft 23. This may, for example, provide for a reduced drag force on the needle cannula 22 as it is being pulled proximally during use. In an alternative embodiment, the inner surface 54 of the arms 48a, 48b may be configured to engage the outer surface 248 of the needle shaft 23.

While in one embodiment, the arms 48a, 48b are biased generally radially outward, in an alternative embodiment, the arms 48a, 48b may be configured to be biased generally radially inward relative to central axis 44. In such an embodiment, the inner surface 54 of arms 48a, 48b may be configured to engage the outer surface 248 of the needle shaft 23 and may be moved generally radially outward due to the presence of the needle cannula 22 extending through inner member 32 (e.g., the needle cannula 22 moves the arms 48a, 48b radially outward against the bias).

Additionally, the locking tabs 158 of the outer member 34 may be biased generally inward relative to central axis 126. More particularly, when in the ready position, and the inner member 32 is in its first position relative to outer member 34, the locking tabs 158 may be configured to engage the bottom wall 80 of groove 78. This engagement may serve a couple of purposes including, for example, providing a resistance force to movement of the inner member 32 relative to the outer member 34 during the initial proximal movement of the needle cannula 22 as it is being withdrawn. The engagement between the locking tabs 158 and groove 78 may further provide an anti-rotation feature between the inner and outer members 32, 34.

As discussed above, the inner and outer members 32, 34 are oriented in a specific manner during assembly so as to provide proper operation of the tip protector 30. Accordingly, it would be undesirable to have relative rotation therebetween during use of the safety catheter 10. For example, it would be undesirable to allow the inner member 32 to rotate relative to outer member 34 with rotation of the needle cannula 22. In that regard, the tip protector 30 may be designed to permit rotation of the needle cannula 22 without causing rotation of the tip protector 30 (i.e., the needle cannula 22 is free to rotate relative to the tip protector 30). Additionally, even if, through friction forces, rotation of the needle cannula 22 would tend to rotate the inner member 32 (or the outer member 34), relative rotation between the inner and outer members 32, 34 is restricted by the interaction of several features. For example, as noted above, engagement of the locking tabs 158 with grooves 78 provides a restriction to relative rotation between the inner and outer members 32, 34. More particularly, if relative rotation between the inner and outer members 32, 34 were initiated, the side edges of the flexible tabs 158 would contact the side walls 82 of grooves 78 and therefore resist the relative rotation.

Additionally, as shown in FIG. 16B, when in the ready position, the raised bosses 74 on the inner member 32 may be received within the cutouts 142 in the outer member 34 such that, for example, the outer surface of the raised bosses 74 is substantially flush with the outer surface of the outer member 34. The invention is not so limited as the raised bosses 74 may extend beyond the periphery of the outer member 34 in alternative embodiments. In any event, if relative rotation between the inner and outer members 32, 34 were initiated, the side abutment surfaces 76 of raised bosses 74 would contact the side edges 148 of cutouts 142 and therefore resist the relative rotation.

In addition to preventing relative rotation between the inner and outer members 32, 34, the raised bosses 74 and cutouts 142 may also resist axial movement of the inner member 32 relative to the outer member 34 in at least one direction. More particularly, the distal abutment surface 76 on raised bosses 74 and distal edge 146 of cutout 142 provide a positive stop that prevents the inner member 32 from axially shifting distally relative to the outer member 34 when in the ready position.

In addition to the above, the safety catheter 10 may be designed to allow the tip protector 30 to rotate relative to the catheter hub 16. However, rotation of the tip protector 30 relative to the catheter hub 16 would similarly not cause relative rotation between the inner and outer members 32, 34 due to the interaction between the features described above. Thus, in accordance with embodiments of the invention, the needle cannula 22 is free to rotate relative to the tip protector 30 and the tip protector 30, is free to rotate relative to the catheter hub 16.

As further shown in FIGS. 16A and 16B, when in the ready position, the spines 194 on needle hub 20 may be disposed about the flange 172 and extension portion 178 that extend beyond the proximal end 230 of the catheter hub 16. Additionally, in one embodiment, the end face 200 of the spines 194 may be configured to engage the proximal end 230 of the catheter hub 16. Moreover, when in the ready position, the needle hub 20 may be configured to engage or alternatively be spaced from the tip protector 30. By way of example, in one embodiment, the inner surface 198 of the spines 194 may engage the outer surface 250 of extension portion 178. Additionally, or alternatively, the taper 202 adjacent the distal end of spines 194 may engage the proximally facing lip 176 of flange 172. Furthermore, the end of distal nose 188 may additionally or alternatively engage the end face 180 of outer member 34.

After the safety catheter 10 is inserted into the artery or vein of the patient, the needle hub 20, and thus the needle cannula 22, may be moved proximally relative to the catheter assembly 12 and tip protector 30. However, the safety catheter 10 is configured such that drag forces imposed on the tip protector 30 due to the proximal movement of the needle cannula 22 are not sufficient to overcome the forces retaining the tip protector 30 to the catheter hub 16. Accordingly, the tip protector 30 remains secured to the catheter hub 16 during at least the initial proximal movement of the needle cannula 22.

Additionally, the drag forces imposed on the inner member 32 of tip protector 30 due to the proximal movement of the needle cannula 22 are not sufficient to axially shift the inner member 32 relative to the outer member 34. In this regard, the engagement between locking tabs 158 and the bottom wall 80 of grooves 78, the resistance to movement of the inner member 32 relative to the outer member 34 due to the generally outwardly biasing of the arms 48a, 48b (e.g., engagement between the raised bosses 74 on arms 48a, 48b and the proximal edge 144 of cutout 142), or other sources, provides a resistive force that is greater than the drag forces imposed on the inner member 32 due to proximal movement of the needle cannula 22. Accordingly, the inner member 32 does not move proximally relative to the outer member 34 during at least this initial proximal movement of the needle cannula 22.

Figure 17:
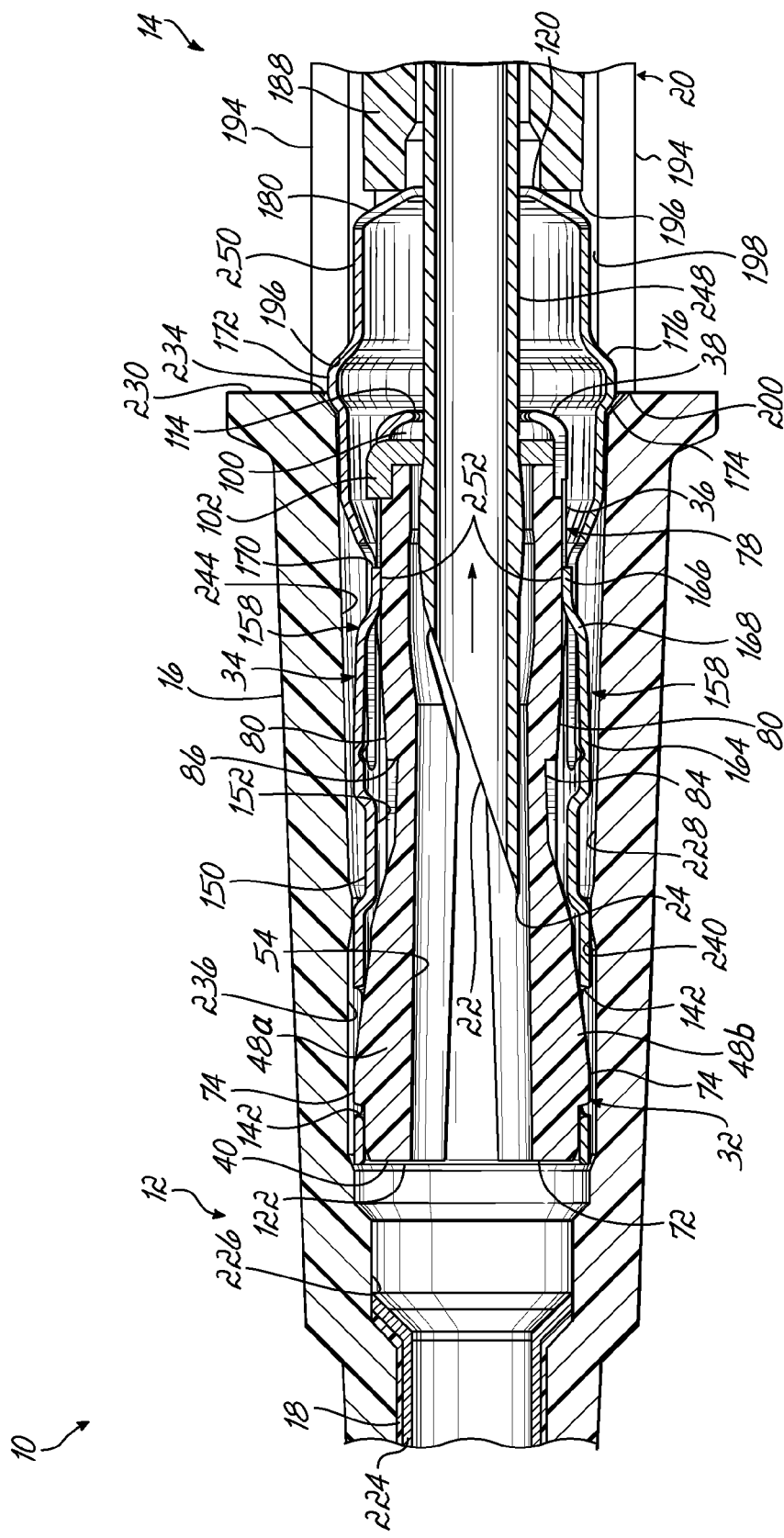
FIG. 17 is a partial cross-sectional view of the safety catheter taken along line 16B-16B (shown in FIG. 16) with the distal tip of the needle cannula disposed in the tip protector.

As the needle hub 20 and needle cannula 22 are moved further in the proximal direction, the distal tip 24 thereof moves proximal of the distal end 122 of the outer member 34 and proximal of the distal end 40 of the inner member 32, which is disposed within the outer member 34. Such a positioning of distal tip 24 relative to inner member 32 and outer member 34 is best illustrated in FIG. 17. Note that although the needle cannula 22 no longer blocks the arms 48a, 48b, the arms 48a, 48b do not move radially inward (due to their outward bias). Thus, at this point, the raised bosses 74 of the inner member 32 remain in the cutouts 142 of the outer member 34. If the arms 48a, 48b were biased generally radially inward toward central axis 44, as in one of the alternative embodiments discussed above, positioning the distal tip 24 within the inner member 32 as shown in these figures would allow the arms 48a, 48b to close radially inward under their own bias due to the absence of the needle cannula 22 between the distal portion of the arms 48a, 48b. However, in such an alternative embodiment, the closing down of the arms 48a, 48b radially inward would not otherwise affect the release of the tip protector 30 from the catheter hub 16 or affect the lack of axially movement of the inner member 32 within the outer member 34.

With reference to FIG. 17, as the needle hub 20 and needle cannula 22 are moved further in the proximal direction, and with the distal tip 24 positioned within the inner member 32 so as to not block the radially inward movement of the arms 48a, 48b, the protuberance 222 is configured to engage the stop washer 102. In this regard, the portion of the needle shaft 23 proximal of protuberance 222 is sized so as to pass through the central aperture 110 in stop washer 102, pass through the opening 116 in the proximal end face 114 of inner member 32, and pass through the opening 182 in the proximal end face 180 of outer member 34. A cross dimension of protuberance 222, however, is sized to be greater than the cross dimension of the central aperture 110 in stop washer 102. Thus, when the protuberance 222 engages the stop washer 102, further proximal movement of the needle cannula 22 relative to the inner member 32 is thereby restricted.

Accordingly, with further proximal movement of the needle hub 20 and needle cannula 22, the engagement between the protuberance 222 and stop washer 102, which is secured within the inner member 32 as described above, causes the inner member 32 to be axially shifted proximally relative to the outer member 34. Because of the holding force between the dimples 127 (or struts 132) and the inner wall 244 of the body member 118, during the axial shifting of the inner member 32 relative to the outer member 34, the outer member 34, and thus the tip protector 30, remains secured to the catheter hub 16. In other words, a proximal force from the needle cannula 22 sufficient to axially shift the inner member 32 proximally relative to the outer member 34 is less than the holding force. In addition to the above, during the axial shifting of the inner member 32 relative to the outer member 34, an inner surface 252 of flexible tabs 158 engages and slides along the bottom wall 80 of groove 78. Additionally, during the axial shifting of the inner member 32 within the outer member 34, the cammed proximal surface of the raised bosses 74 engage the proximal edge 144 of cutouts 142 and causes the arms 48a, 48b to move generally radially inward so as to essentially close down against their bias such that the raised bosses 74 are no longer received in the cutouts 142, but are within the confines of the outer member 34 proximal of cutouts 142. Moreover, the raised bosses 74 and the indentations 150 are generally axially aligned such that the axial shifting of the inner member 32 away from its first position causes the raised bosses 74 to contact the engaging surfaces 152 of the indentations 150, which project into the passageway 124 of the outer member 34. This engagement, in turn, causes the arms 48a, 48b to close down (i.e., move radially inward toward each other) even further.

Regardless of the particular embodiment, it should be recognized that the drag forces imposed on the outer member 34 by axial shifting of the inner member 32 is less than the holding force imposed between the projecting portions of outer member 34 and the inner wall 244 catheter hub 16. Notably, the holding force remains substantially constant irrespective of the position of the inner member 32 between the first and second positions. This substantially constant holding force allows the inner member 32 to be axially shifted relative to the outer member 34 without the outer member 34 releasing from the catheter hub, and thus prevents the tip protector 30 from being prematurely pulled proximally out of the catheter hub 16.

Figure 18:
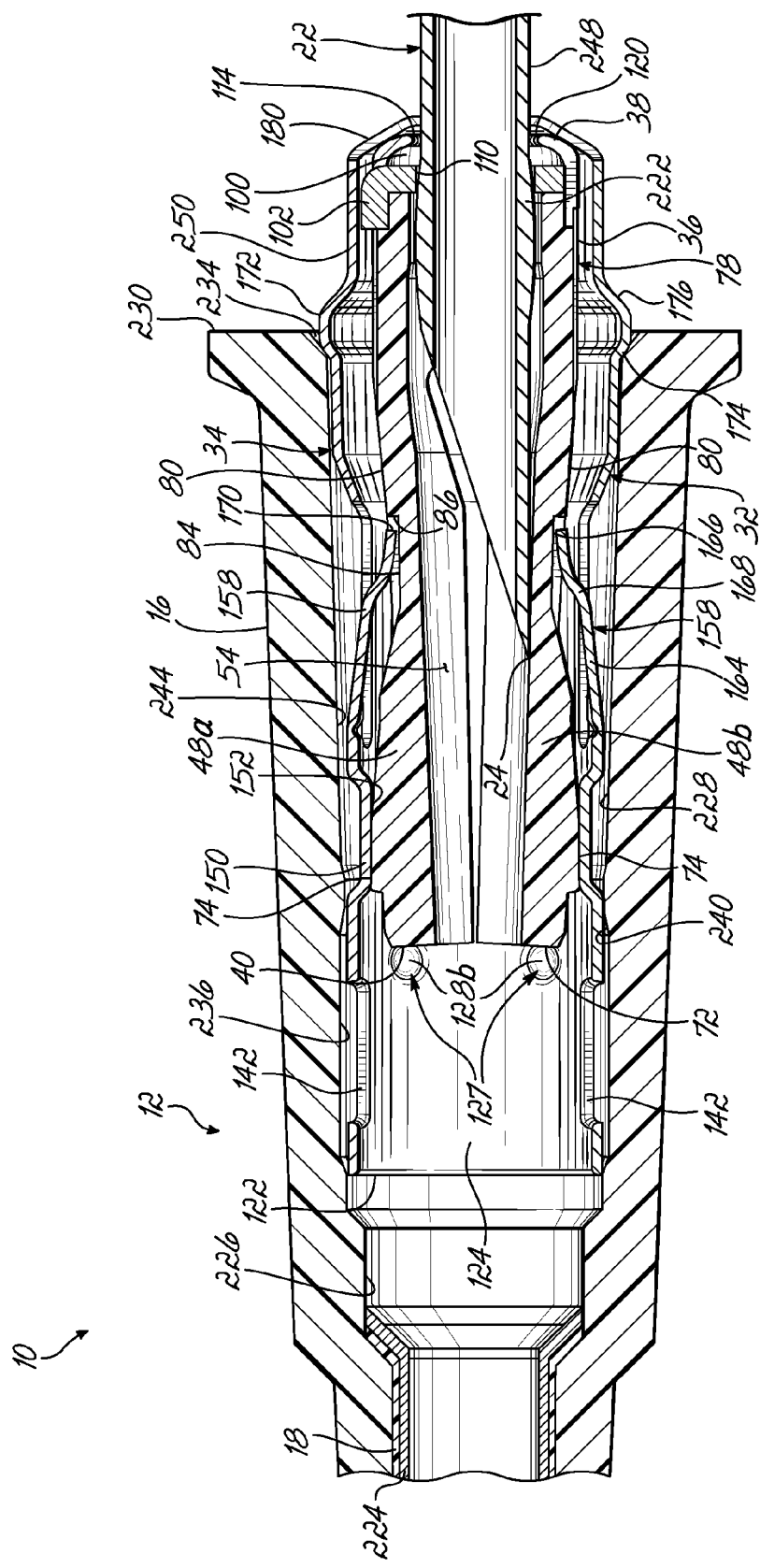
FIG. 18 is a partial cross-sectional view of the safety catheter in the protected position, taken along line 16B-16B (shown in FIG. 16), wherein the inner member is in a second position relative to the outer member.

With reference to FIG. 18, as the inner member 32 continues to be axially shifted proximally within the outer member 34, the proximal tab portion 166 of locking tabs 158 drops into cavity 84 formed in the bottom wall 80 of groove 78 due to the generally inward bias of locking tabs 158. When the proximal tab portion 166 drops into cavity 84, distal axial shifting of the inner member 32 relative to the outer member 34 is restricted by engagement between the contacting edge 170 of locking tabs 158 and the first end wall 86 of cavity 84 (i.e., the inner member 32 cannot be pushed out of the outer member 34). Furthermore, when the proximal tab portion 166 drops into cavity 84, the proximal end 38 of the inner member 32 may be in close proximity to the proximal end 120 of the outer member 34. In this regard, the opening 182 in the proximal end 120 of outer member 34 is sized so as to prevent the inner member 32 from passing therethrough.

Thus, the proximal end 120 of outer member 34 operates as a stop that prevents further proximal axial shifting of the inner member 32 relative to the outer member 34. In this way, when the proximal tab portion 166 drops into cavity 84, proximal and distal axial shifting of the inner member 32 relative to the outer member 34 is substantially restricted and the inner and outer members 32, 34 are essentially locked together. In this position, it will be seen that the inner member 32 is in a second or proximal position relative to the outer member 34 and the safety catheter 10 may be considered to be in the fired position as the distal tip 24 of the needle cannula 22 is secured within the tip protector 30, and any further force imposed on the inner member 32 with proximal movement of the needle cannula 22 will be translated to the outer member 34 to try to overcome the holding force between the tip protector 30 and the catheter hub. In that regard, the locking tabs 158 and cavity 84 operate as a locking mechanism that restricts axial shifting of the inner member 32 relative to the outer member 34 in the distal direction. Similarly, the sizing of opening 182 in the proximal end 120 of outer member 34, so as to block passage of inner member 32 therethrough, may also operate as a locking mechanism to restrict proximal axial shifting of the inner member 32 relative to the outer member 34.

In one embodiment, the outside surface of proximal end face 114 of inner member 32 may engage the inside surface of proximal end face 180 of outer member 34 at nearly the same time that the proximal tab portion 166 drops into cavity 84, such that there is essentially no play between the inner and outer members 32, 34 when the proximal tab portion 166 drops into cavity 84. As illustrated in FIG. 18, the proximal end 38 of the inner member 32 may be slightly spaced from the proximal end 120 of the outer member 34 when the distal tab portion 164 drops into cavity 84. In such an embodiment, additional proximal axial shifting of the inner member 32 relative to the outer member 34 may be permitted before the proximal ends 38, 120 of the inner and outer members 32, 34, respectively, engage each other. In other words, although the inner and outer members 32, 34 are essentially locked together, a certain amount of play may exist between the two members 32, 34 after being locked together.

However, upon further withdrawal of the inner member 32, the outer member may move in the proximal direction such that the position of the needle assembly 14 is as shown in FIG. 19. In any event, the inner member 32 is positioned so as to shield the distal tip 24 of needle cannula 22. In order for the outer member 34 to be shifted in the proximal direction however, the needle assembly 14 must be pulled or otherwise directed towards the proximal direction such that the projecting portions move away from the retention groove 240. Because of the fixed manner of the projecting portions, it is understood that such movement thereof away from the retention groove 240 may require the retention groove 240 to yield as the projecting portions traverse or move out of the retention groove 240. More particularly, it is understood that some of the material that makes up the catheter hub 16 adjacent the retention groove 240 may experience some amount of plastic deformation as the projecting portions move out of the retention groove 240. To this end, a sufficiently high force has to be imposed as the needle assembly 14 is pulled or otherwise directed towards the proximal direction such that the contoured surface 129b of the dimples 127 (or contoured surface 135 of struts 132) cams against the proximal edge 241 and as understood plastically deforms the blocking aspect of the catheter hub 16, including, for example, the proximal edge 241. The contoured surface 129b (or contoured surface 135) advantageously contributes to the holding force that, on the one hand, secures the tip protector 30 to the catheter hub 16 during normal use of the safety catheter 10, and on the other hand, allows the tip protector 30 to be pulled out of the catheter hub 16 through plastic deformation of an aspect of the catheter hub and without an unduly high tug force, which might be undesirable for clinicians. Alternatively and/or additionally, the proximal edge 241 may be contoured, sloped, or otherwise shaped to provide a desired holding force. In other words, the configuration of the projecting portions alone or in combination with the proximal edge 241 may be altered to allow variation in the holding force (and consequently the pulling force to effectuate release) that ultimately causes plastic deformation of the catheter hub 16.

FIG. 19 illustrates the needle assembly 14 fully withdrawn from the catheter assembly 12 (not shown), which remains in fluid communication with the vasculature of the patient. As shown, the distal portion of the needle cannula 22, including the distal tip 24 thereof, is shielded by tip protector 30 while more proximal portions of the needle shaft 23 are exposed. Furthermore, the tip protector 30 is designed to prevent or significantly reduce the chance or likelihood of re-exposing the distal tip 24 of the needle cannula 22. As discussed above, once the locking tabs 158 drop into cavity 84, the inner and outer members 32, 34 are essentially locked together and tip protector 30 is also essentially locked onto needle cannula 22. In that regard, should the needle cannula 22 be pulled proximally relative to the tip protector 30 (e.g., such as by grabbing the outer member 34 thereof with one hand and pulling proximally on the needle hub 20 with the outer hand), the protuberance 222 will act on stop washer 102, which in turn acts on inner member 32. However, as noted above, the proximal end 38 of inner member 32 is engaged with or is in near engagement with the proximal end 120 of outer member 34 so as to effectively prevent the needle cannula 22 from being pulled proximally out of the tip protector 30.

Similarly, should the needle cannula 22 be pushed distally relative to the tip protector 30 (e.g., such as by grabbing the outer member 34 thereof with one hand and pushing distally on the needle hub 20 with the outer hand), there may be some slight distal movement of the needle cannula 22 relative to tip protector 30. However, with reference to FIG. 18, as the needle cannula 22 moves distally, the needle cannula 22 will contact the inner surface 54 of arms 48a, 48b. More particularly, when the inner member 32 is in its second position relative to the outer member 34, the cross dimension of passageway 42 along a distal portion thereof is smaller than the cross dimension of the needle shaft 23 adjacent the distal tip 24. Accordingly, when in the second position, the passageway 42 along distal tapered bore portions 92 is sized so as to block the path of needle cannula 22 (i.e., the size of the distal tapered bore is smaller than the needle cannula 22). Additionally, when in the second position, the arms 48a, 48b of inner member 32 are constrained by the outer member 34 (e.g., engagement between the engaging surfaces 152 of indentations 150 and the raised bosses 74), and thus, the arms 48a, 48b are not capable of flexing generally radially outward so as to increase the size of passageway 42 and allowing the needle cannula 22 to pass therethrough.

Furthermore, when distal movement of the needle cannula 22 relative to the inner member 32 has been blocked, depending on the particular embodiment, it may be possible to axially shift the inner member 32 distally relative to the outer member 34. For example, if there is some slight play between the inner and outer members 32, 34 when they are essentially locked together, such relative axial shifting therebetween may be possible. However, any such relative axial shifting is small and distal movement of the inner member 32 relative to the outer member 34 is eventually restricted by engagement of the contacting edge 170 of locking tabs 158 and the first end wall 86 of cavity 84. Accordingly, even though there may be slight relative movement between the needle cannula 22 and tip protector 30, ultimately the distal tip 24 of the needle cannula 22 is effectively prevented from re-emerging by pushing the needle cannula 22 distally out of the tip protector 30.

FIGS. 20-30 illustrate various views of an outer member similar to that shown in FIGS. 6, 7, and 8. FIGS. 31-41 illustrate various views of an alternative outer member similar to that shown in FIGS. 6A, 7A, and 8A.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. Thus, the invention in its broader aspects is, therefore, not limited to the specific details, representative apparatus and method, and illustrative examples shown and described. Accordingly, departures may be made from such details without departing from the spirit or scope of the general inventive concept. While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art.

Having described the invention, what is claimed is:

1. A safety catheter, comprising:
    a catheter hub defining an interior cavity and a catheter tube extending distally of the catheter hub;
    a needle hub and a needle cannula extending distally thereof, the needle cannula having a distal tip; and
    a tip protector for shielding the distal tip comprising an outer member releasably engaged with the interior cavity of the catheter hub to provide a holding force of the tip protector to the catheter hub, wherein the outer member includes a generally fixed radially outwardly projecting portion to provide the holding force, and an inner member axially received within the outer member, the needle cannula being received in the inner and outer members, the inner member configured to be axially shiftable relative to the outer member between a distal position wherein the distal tip extends distally of the tip protector, and a proximal position wherein the distal tip is within the outer member, wherein the holding force of the outer member to the interior cavity of the catheter hub remains substantially constant irrespective of the position of the inner member between the distal and proximal positions;
    wherein the projecting portion has an outer surface defining a radially outermost portion and a contoured surface extending from the radially outermost portion;
    wherein the interior cavity of the catheter hub includes a proximal edge and a retention groove extending radially outwardly of the proximal edge; and
    wherein the contoured surface of the projecting portion cams against the proximal edge with proximal movement of the outer member so as to plastically deform the catheter hub and effectuate release of the tip protector from the catheter hub.

2. The safety catheter of claim 1, wherein the projecting portion is received in the retention groove to provide the holding force of the outer member to the interior cavity of the catheter hub.

3. The safety catheter of claim 1, wherein the outer member includes a generally cylindrical body member having an outer surface and an inner surface, the projecting portion extending radially outwardly of the outer surface of the body member.

4. The safety catheter of claim 3, wherein the outer surface of the projecting portion is continuous with the outer surface of the body member.

5. The safety catheter of claim 3, wherein the projecting portion includes an inner surface, wherein the inner surface of the projecting portion is continuous with the inner surface of the body member.

6. The safety catheter of claim 3, wherein the projecting portion includes a plurality of discrete dimples formed in the body member.

7. The safety catheter of claim 1, wherein the projecting portion includes an inner surface, the inner and outer surfaces of the projecting portion have a substantially similar contour.

8. The safety catheter of claim 1, wherein the outer member includes a generally cylindrical body member having an outer surface and an inner surface, a cutout through the body member, and a strut extending across the cutout, the strut including a strut portion extending radially outwardly of the outer surface to define the projecting portion.

9. The safety catheter of claim 8, wherein the body member includes a pair of struts extending across the cutout, each strut including a strut portion extending radially outwardly of the body member to define the projecting portion.

10. The safety catheter of claim 8, wherein the outer member includes a central axis and the strut extends across the cutout in a direction generally parallel to the central axis.

11. The safety catheter of claim 1, wherein the inner member is axially received entirely within the outer member.

12. The safety catheter of claim 1, wherein the needle cannula and the inner member cooperate to axially shift the inner member from the distal position to the proximal position as the needle cannula is proximally withdrawn, a portion of the inner member sized to prevent proximal removal from the outer member such that in the distal position of the inner member, a proximal force from the needle cannula sufficient to axially shift the inner member from the distal position toward the proximal position is less than the holding force.

13. A safety catheter, comprising:
    a catheter hub and a catheter tube extending distally thereof;
    a needle hub and a needle cannula extending distally thereof, the needle cannula having a distal tip; and
    a tip protector for shielding the distal tip comprising an outer member releasably engaged with an interior cavity of the catheter hub to provide a holding force of the tip protector to the catheter hub, and an inner member axially received within the outer member, the needle cannula being received in the inner and outer members, the inner member configured to be axially shiftable relative to the outer member between a distal position wherein the distal tip extends distally of the tip protector, and a proximal position wherein the distal tip is within the outer member, wherein the holding force of the outer member to the interior of the catheter hub remains substantially constant irrespective of the position of the inner member between the distal and proximal positions, and wherein the inner member is positioned in the catheter hub at least when in the distal position;

wherein the projecting portion has an outer surface defining a radially outermost portion and a contoured surface extending from the radially outermost portion;

wherein the interior cavity of the catheter hub includes a proximal edge and a retention groove extending radially outwardly of the proximal edge; and wherein the contoured surface of the projecting portion cams against the proximal edge with proximal movement of the outer member so as to plastically deform the catheter hub and effectuate release of the tip protector from the catheter hub.

14. The safety catheter of claim 13, the outer member includes a generally fixed radially outwardly projecting portion, wherein the projecting portion is received in the retention groove to provide the holding force of the outer member to the interior of the catheter hub.

15. The safety catheter of claim 13, wherein the outer member includes a generally cylindrical body member having an outer surface and an inner surface, the projecting portion extending radially outwardly of the outer surface of the body member.

16. The safety catheter of claim 15, wherein the projecting portion includes an inner surface, wherein the outer surface of the projecting portion is continuous with the outer surface of the body member.

17. The safety catheter of claim 16, wherein the inner surface of the projecting portion is continuous with the inner surface of the body member.

18. The safety catheter of claim 17, wherein the inner and outer surfaces of the projecting portion have a substantially similar contour.

19. The safety catheter of claim 15, wherein the projecting portion includes a plurality of discrete dimples formed in the body member.

20. The safety catheter of claim 13, wherein the outer member includes a generally cylindrical outer wall having an outer surface and an inner surface, a cutout through the outer wall, and a strut extending across the cutout, the strut including a strut portion extending radially outwardly of the outer surface to define the projecting portion.

21. The safety catheter of claim 20, wherein the outer member includes a pair of struts extending across the cutout, each strut including a strut portion extending radially outwardly of the outer surface to define the projecting portion.

22. The safety catheter of claim 20, wherein the outer member includes a central axis and the strut extends across the cutout in a direction generally parallel to the central axis.

23. The safety catheter of claim 13, wherein the inner member is axially received entirely within the outer member.

24. The safety catheter of claim 13, wherein the needle cannula and the inner member cooperate to axially shift the inner member from the distal position to the proximal position as the needle cannula is proximally withdrawn, a portion of the outer member sized to prevent proximal removal of the inner member from the outer member such that in the distal position of the inner member, a proximal force from the needle cannula sufficient to axially shift the inner member from the distal position toward the proximal position is less than the holding force.

* * * * *

UNITED STATES PATENT AND TRADEMARK OFFICE
CERTIFICATE OF CORRECTION

PATENT NO. : 9,555,221 B2  
APPLICATION NO. : 14/250042  
DATED : January 31, 2017  
INVENTOR(S) : Koehler et al.

It is certified that error appears in the above-identified patent and that said Letters Patent is hereby corrected as shown below:

In the Claims

In Column 23 Line 22, after "Claim 13", please insert --wherein--.

Signed and Sealed this
Fourth Day of April, 2017

Michelle K. Lee
*Director of the United States Patent and Trademark Office*